US007342090B1

(12) United States Patent
Pai et al.

(10) Patent No.: US 7,342,090 B1
(45) Date of Patent: Mar. 11, 2008

(54) FAB-EPITOPE COMPLEX FROM THE HIV-1 CROSS-NEUTRALIZING MONOCLONAL ANTIBODY 2F5

(75) Inventors: Emil F. Pai, Toronto (CA); Michel H. Klein, Toronto (CA); Pele Chong, Richmond Hill (CA); Arthur Pedyczak, Pickering (CA)

(73) Assignees: University of Toronto, Toronto, Ontario (CA); Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 09/958,605

(22) PCT Filed: Apr. 5, 2000

(86) PCT No.: PCT/CA00/00358

§ 371 (c)(1),
(2), (4) Date: May 1, 2002

(87) PCT Pub. No.: WO00/61618

PCT Pub. Date: Oct. 19, 2000

Related U.S. Application Data

(63) Continuation of application No. 09/289,942, filed on Apr. 13, 1999, now Pat. No. 6,482,928.

(51) Int. Cl.
*A61K 38/12* (2006.01)
*A61K 39/385* (2006.01)
*C07K 7/64* (2006.01)

(52) U.S. Cl. ........................ 530/317; 530/329; 514/11; 514/16

(58) Field of Classification Search ..................... None
See application file for complete search history.

(56) References Cited

U.S. PATENT DOCUMENTS 5,831,034 A 11/1998 Katinger et al.

FOREIGN PATENT DOCUMENTS

WO WO 95/07354 A 3/1995
WO WO 96/02273 A 2/1996

OTHER PUBLICATIONS

Muster, T., et al., A conserved neutralizing epitope on gp41 of human immunodeficiency virus type 1, J. Virol., 67, 6642-6647 (1993).
Muster, T., et al., Cross-neutralizing activity against divergent human immunodeficiency virus type 1 isolates induced by the gp41 sequence ELDKWAS. J. virology, 68, 4031-4034 (1994).
Purtscher, M., et al., A broadly neutralizing human monoclonal antibody against pg41 of human immunodeficiency virus type 1 (HIV-1) AIDS Res. And Human Retroviruses, 10, 1651-1658 (1994).
Conley, A.J., et al., Neutralization of divergent human immunodefidiciency virus type 1 varints and primary isolates by IAM-41-2F5, an anti-gp41 human monoclonal antibody. Proc. Natl. Acad. Sci. USA, 91, 3348-3352(1994).
Trkola, A., et al., Cross-clade neutralization of primary isolates of human immunodeficiency virus type 1 by human monoclonal antibodies and tetrameric CD4-IGG. J. Virology, 69, 6609-6617 (1995).
Burton D.R., A vaccine for HIV type 1: The antibody perspective. Proc. Natl. Acad. Sci. USA, 94, 10018-10023 (1997).
Ernst W., et al., Baculovirus surface display: Construction and screening of a eukaryotic epitope library, Nucl. Acids Res. 26, 1718-1723 (1998).
Cook, J., et al., Recombinant antibodies with conformationally constrained HIV type 1 epitope inserts elicit glycoprotein 160-specific antibody responses in vivo. AIDS Res. Human Retroviruses, 13, 449-460 (1997).
Chan, D.E. & Kim, P.S., HIV entry and its inhibition, Cell, 93, 681-684 (1998).
Navaza, J., AMoRe—an automated package for molecular replacement, Acta Crystallogr., A50, 157-163 (1994).
Jeffrey, P.D., et al., The X-ray structure of anti-tumour antibody in complex with antigen. Nature Struct. Biol., 2, 466-471 (1995).
Brunger, A.T., et al., Crystallography and NMR system: A new software system for macromolecular structure determination, Acta Cryst. D, 54, 905-921 (1998).
Kraulis, P.J., MOLSCRIPT: a program to produce both detailed and schematic plots of protein structure, J., Applied Cryst., 24, 946-950 (1991).
Merritt, E.A. & Murphy, M.E.P. Raster 3D Version 2.0, A program for photoreolislic Molecular graphics. Acta Cryst. D50, 869-873, (1994).
Jones, T.A. et al., Improved methods for building protein models in electron density maps and the location of errors in these models . . . Acta Cryst. A47, pp. 110-119 (1991).
Evans, S.V., SETOR: hardware-lighted three-dimensional solid model representations of macromolecules, J. Mol. Graph., 11, 134-8, (1993).
Riddles et al., Reassessment of Ellman's Reagent (1983), Methods Enzym. vol. 91pp. 49-60.
Chong et al., Structural and functional analysis of the S1 subunit of pertussis toxin using synthetic peptides. (1991), Mol. Immunol. vol. 28, pp. 239-245.
Mascola, J.R., et al. Potent and synergistic Neutralization of human immunodeficiency virus (HIV) type 1 primary isolates by hyperimmune anti-HIV immunolobulin combined with monoclonal antibodies 2F5 and 2G12. J. Virology, 71, 7198-7206 (1997).

(Continued)

*Primary Examiner*—Marianne P. Allen
(74) *Attorney, Agent, or Firm*—Michael I. Stewart; Sim & McBurney

(57) ABSTRACT

The crystal structure of the Fab' fragment of Mab 2F5, a potent neutralizer of both laboratory strains and primary clinical isolates of most clades of HIV-1, both uncompleted and complexed with the largely conserved peptide sequence ELDKWAS of the viral envelope protein gp41, has been elucidated and the characteristics of peptide-protein interactions determined. Having regard to such determination, the peptide-mimetics are constrained in the three-dimensional structure to provide an increased immunogenicity to the epitope sequence.

4 Claims, 4 Drawing Sheets

OTHER PUBLICATIONS

Eckhart, L., et al., Immunogenic presentation of a conserved gp41 epitope of human immunodeficiency virus type 1 on recombinant surface antigens of hepatitus B. virus. J. of General Virology, 77, 2001-2008 (1996).

Kunert, R., et al., Molecular characterization of five neutralizing anti-HIV type 1 antibodies: identification of nonoconventional D segments in the human monoclonal antibodies 2G12 and 2F5, AIDS Res. and Human Retroviruses, 14, 1115-1128, (1998).

Richardson, J.S., The anatomy and taxonomy of protein structure, Adv. Protein Chem., 34, 167-339, (1981).

Gallaher, W.R., et al., A general model for the transmembrane proteins of HIV and other retroviruses. AIDS Res. And Human Retroviruses, 5, 431-440 (1989).

Weissenhom, W., et al., Atomic structure of the ectodomain from HIV-1 gp41. Nature, 387, 426-430 (1997).

Tan, K., et al., Atomic structure of a thermostable subdomain of HIV-1 gp41. Proc. Natl. Acad. Sci. USA, 94, 12303-12308 (1997).

Chan, D., et al., Core structure of gp41 from the HIV envleope glycoprotein. Cell, 89, 263-273 (1997).

Malashkevich, V.N., et al., Crystal structure of the simian immunodeficiency virus (SI) gp41 core: Conserved helical interactions underlie the broad inhibitory activity of gp41 peptides, Proc. Natl. Acad. Sci. USA, 95, 9134-9139 (1998).

Yang, Z.N., et al., High resolution structure of simian immunodeficiency virus gp41 ectodomain, Abstracts, American Crystallographic Association Annual Meeting, 1998.

Caffrey, M., et al., Three-dimensional solution structure of the 44 kDa ectodomain of SIV gp41, the EMBO J., 17, 4572-4584 (1998).

Lim L., et al., The three-dimensional structure of Schistosoma japonicum glutathione S-transferase fused with a six-amino acid conserved neutralizing epitope of gp41 from HIV. (1994) 3, 2233-2244.

FAB-EPITOPE COMPLEX FROM THE HIV-1 CROSS-NEUTRALIZING MONOCLONAL ANTIBODY 2F5

REFERENCE TO RELATED APPLICATIONS

This application is a National Phase application under 35 USC 371 of PCT/CA00/00358 filed Apr. 5, 2000 which claims priority from and is a continuation of U.S. patent application No. 09/289,942 filed Apr. 13, 1999 (now U.S. Pat. No. 6,482,928).

FIELD OF INVENTION

This invention relates to crystallography and immunology, and, in particular, to the elucidation, for the first time, of the three-dimensional structure of the Fab' fragment of monoclonal antibody 2F5.

BACKGROUND TO THE INVENTION

The monoclonal antibody (Mab) 2F5 is a potent neutralizer of both laboratory strains and primary isolates of most clades of HIV-1, reacting with the largely conserved peptide sequence ELDKWAS (SEQ ID No: 1) of the virus envelope protein gp41, sometimes called the Katinger Epitope (refs. 1 to 7. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). As such, Mab 2F5 is of major interest in the development of an HIV-1 vaccine. Based on studies of immunogenic presentation, the antigenicity of the epitope sequence was concluded to be contingent upon its molecular context (ref. 8).

SUMMARY OF THE INVENTION

In accordance with the present invention, there is provided the three-dimensional structure of the Fab' fragment of Mab 2F5, both uncomplexed and with bound epitope. In the complexed crystalline structure, the seven amino acid sequence (ELDKWAS) forms a slightly distorted β turn, with the central DKW core accounting for the majority of protein/peptide interactions, as discussed below.

As can be seen from the detailed analysis provided herein, the slightly-distorted β turn is stabilized by hydrogen bonds from aspartate backbone and sidechain to alanine and tryptophan amides respectively. In the three-dimensional structure, tryptophan and lysine sidechains of the epitope are stacked and parallel.

The elucidation of these three-dimensional structures enables there to be constructed, as set forth herein, peptide-mimetics constrained in the same β-turn-like configuration as seen in the crystal structure of the complex, which would be expected to increase the imrnmunogenicity of the epitope sequence.

Accordingly, in one aspect of the invention, there is provided an isolated crystal of the Fab' fragment of monoclonal antibody 2F5. The isolation of the crystalline form of the Fab'2F5 fragment enables the three-dimensional structure of such form of the fragment to be determined and such structure is shown in FIG. 1, described below. Certain characterizing parameters have been determined for the crystal structure, as set forth in Table 2 below.

The isolated crystal may be grown in space group $P2_1$, $2_1$,$2_1$ with cell dimensions a=63.6 Å; b=76.4 Å; c=93.4 Å, although the crystals may be grown in another space group with its own unique cell dimensions. The crystalline form of the Fab'2F5 may have the atomic coordinates deposited on Apr. 9, 1999 with the Protein Data Bank under Accession No. 2F5A.

Fab'2F5 molecules organized in the isolated crystal provided herein possess a third hypervariable (V3) loop of the heavy chain comprising amino acid residues H98 to H120, as seen in Table 1 below, which has a three-dimensional structure as shown in FIG. 4, described below and atomic coordinates as shown in Table 3 below.

In accordance with a further aspect of the present invention, there is provided an isolated crystal of the Fab' fragment of monoclonal antibody 2F5 complexed with a peptide having the amino acid sequence ELDKWAS (SEQ ID No: 1) or a finctional analog thereof. The solution of the crystal form of the complex enables the three-dimensional structure of such form of the complex to be determined and the detail of the binding site of the peptide to the Fab' fragment is shown in FIG. 3, described below. Certain characterizing parameters have been determined for the crystal structure of the complex, as set forth in Table 2 below.

The isolated crystal complex may be grown in space group $P2_12_12_1$ with cell dimensions a=58.0 Å; b=65.0 Å; c=175.6 Å, although the crystal complex may be grown in another space group with its own unique cell dimensions. The crystalline form of the complexed form of the Fab'2F5 may have the atomic coordinates deposited with the Protein Data Bank under Accession No. 2F5B on Apr. 9, 1999.

The functional analog of the amino acid sequence ELDKWAS (SEQ ID No: 1) may be one in which lysine is replaced by arginine and/or one in which tryptophan is replaced by tyrosine, phenylalanine or uncharged histadine. One example of such functional analog is ELDRWAS (SEQ ID No: 2).

The elucidation of the crystal structure of the Fab'2F5 fragment when bound to the peptide ELDKWAS (SEQ ID No: 1), provides details of the actual conformation of the peptide epitope when it is bound to the antibody, which will be the same, irrespective of the kind of crystal which is analyzed.

The information which is provided concerning the conformation of peptide epitope then provides the basis for the provision of peptide analogs, peptide mimetics and other antigens which are potentially useful as components of an anti-HIV vaccine.

Accordingly, in another aspect of the present invention, there is provided a synthetic peptide which binds to monoclonal antibody 2F5 and which is constrained to provide a three-dimensional structure corresponding to that for the peptide ELDKWAS (SEQ ID No: 1) shown in FIG. 3.

This synthetic peptide may contain the amino acid sequence DKW or a functional analog thereof and may be constrained in the slightly distorted β-turn configuration of the three-dimensional structures with the tryptophan and lysine residue chains stacked and parallel, as seen in FIG. 3 and as discussed in more detail below.

The analysis of the three-dimensioned conformation of the epitope indicates that at least one of the tryptophan and lysine sidechains may be substituted by an amino acid which retains the peptide-protein interaction shown in FIG. 3, which also binds to the Mab. For example, arginine (R) may be used in place of lysine (K) and tyrosine (Y), phenylalanine (F) and uncharged histadine (H) may be used in place of tryptophan (W). Peptides wherein one or more of such amino acid substitution is effected are peptides which contain a "functional analog" of the amino acid sequence DKW, as the term is understood herein, in that the peptide still binds to the monoclonal antibody 2F5.

The synthetic peptide provided herein may be constrained in the required conformation by any convenient means. For example, a disulphide bridge may be used to maintain the amino acid sequence DKW or analogs thereof in the respective orientation of two amino acid residues as shown in FIG. 3. Such disulphide bridge may be provided between cysteine residues in the synthetic peptide ECDKWCS (SEQ ID No.: 3).

Alternatively, a lactam bond may be used to maintain the amino acid sequence DKW or functional analogs thereof in the respective orientation of the amino acid residues as shown in FIG. 3. Such lactam bond may be formed between diaminopropionic acid (Dap) and glutamate (E) residues in the synthetic peptide EdapDKWES (SEQ ID No.: 4) or EEDKWDapS (SEQ ID No.: 5).

It is well known that the immunogenicity of peptides may be enhanced by conjugation to carrier molecules, such as proteins, including diphtheria toxoid, tetanus toxoid or an outer membrane protein of *Haemophilus*. Such carrier protein may be linked to the peptide.

There is also provided, in an additional aspect of the invention, a method of making a peptide binding to monoclonal antibody 2F5, which comprises co-crystallizing a Fab' fragment of the monoclonal antibody 2F5 with a peptide having the amino acid sequence ELDKWAS (SEQ ID No.: 1) or functional analog thereof to form a crystalline complex; analyzing the crystalline complex to determine the three-dimensional orientation of the bound peptide in relation to the Fab' fragment; and synthesizing a peptide containing at least amino acids DKW or functional analogs thereof constrained in the determined three-dimensioned orientation.

The functional analog of the peptide containing at least amino acids DKW is one which still binds to the monoclonal antibody 2F5. Functional analogs also extend to known analogs of the ELDKWAS motif, including those of the formula $X_1LDKWX_2S$ wherein $X_1$ is E, A, G or Q and $X_2$ is A or T (SEQ ID No.: 8).

BRIEF DESCRIPTION OF THE DRAWINGS

The file of this patent application contains drawings executed in color, namely FIGS. 1 to 4. Copies of this patent with color drawing(s) will be provided by the Patent and Trademark Office upon request and payment of the necessary fee.

GENERAL DESCRIPTION OF INVENTION

Figure 1:
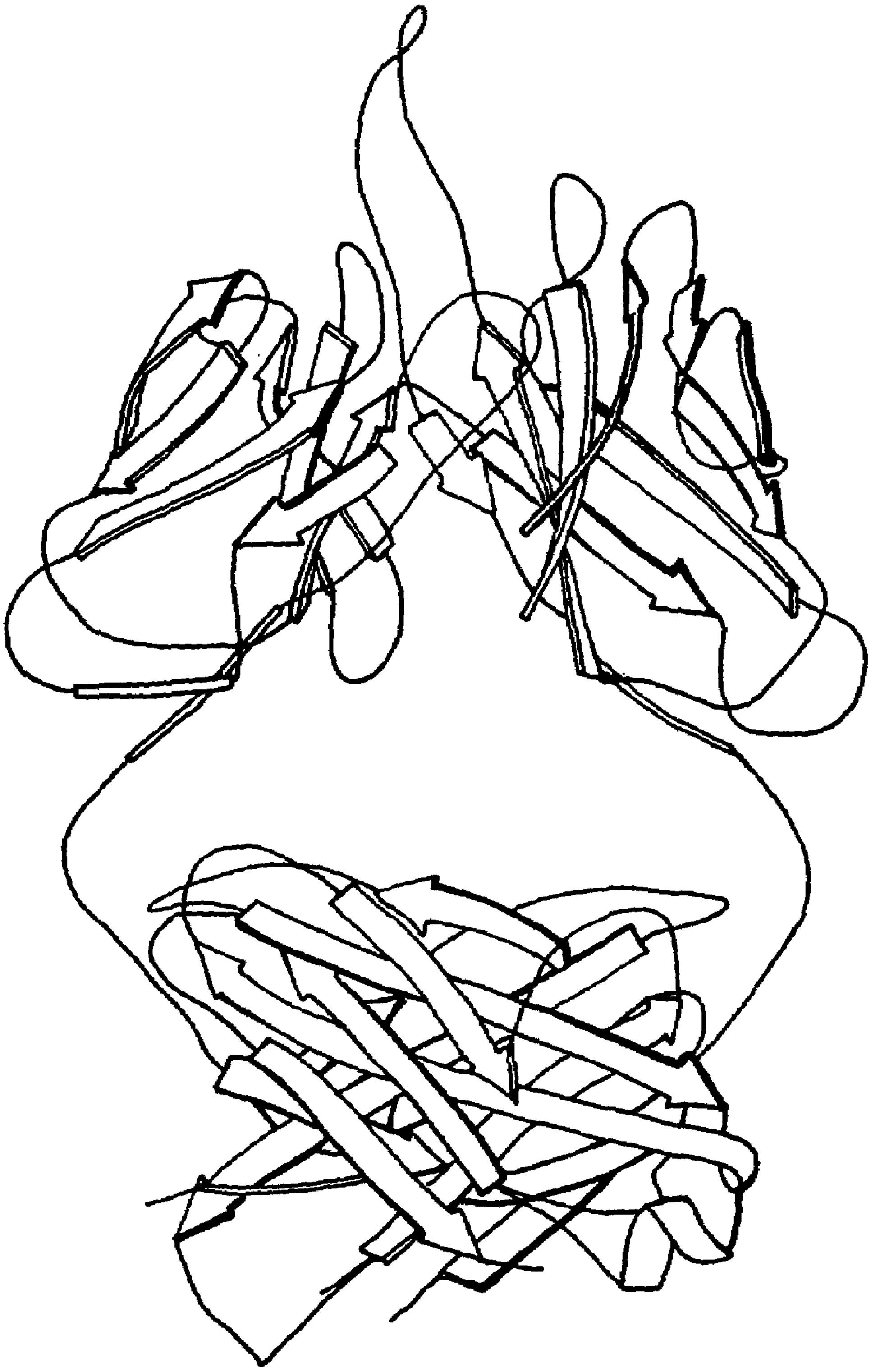
FIG. 1 is a colored ribbon diagram of crystalline Fab'2F5, showing the heavy chain in purple, the light chain in blue and the elongated VH3 loop (colored in gold) extending from the protein surface, as generated by MOLSCRIPT (ref. 27) and Raster 3D (ref. 28)
Figure 4:
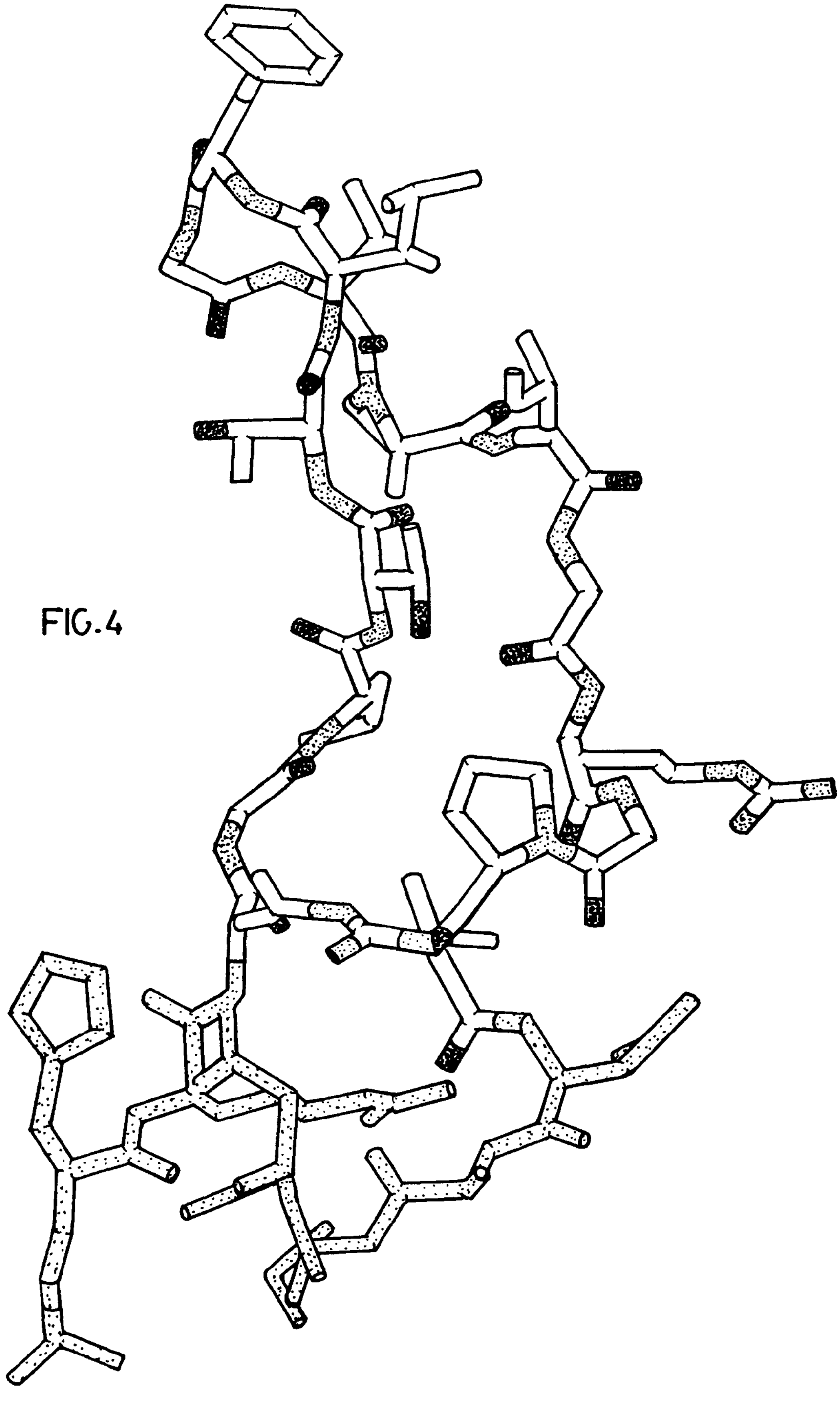
FIG. 4 is a color representation of the third hypervariable loop of the heavy chain of Fab'2F5 complex comprising amino acid residues H98 to H120, as generated using the program SETOR (ref. 30). The residues are colored by atom type.

The crystalline structure of the Fab' fragment of Mab 2F5 (IgG) was solved at 2.05 Åresolution by molecular replacement and adopts the standard immunoglobulin fold. A salient feature of the structure is the elongated (22 amino acids) hypervariable loop 3 of the heavy chain (V-H3, ref. 9), which comprises amino acid residues H98 to 120 and extends away from the protein surface, as can be seen from the ribbon diagram of FIG. 1. The V-H3 loop is shown in detail in FIG. 4. The atomic coordinates of the V-H3 loop are given in Table 3.

In the structure of the Fab'2F5 complex with bound epitope, refined at 2.0 Å, this loop is well-defined by clear electron density. In the uncomplexed form, while the V-H3 region is less clear, loops at the C-terminal regions of the heavy chain constant domain, including the C-termini of both chains, were better resolved. Conformations from the better-defined electron density were used as templates for building the other model. The refined models comprise residues L1 to L214 of the light chain and residues H1 to H146 and H151 to H235 of the heavy chain plus ordered water molecules. The amino acid sequences of the light chain (SEQ ID No.: 6) and heavy chain (SEQ ID No.: 7) of Fab'2F5 are shown in Table 1 below. For the structure of the complex, P1 to P7 are the residues of the peptide. The H147 to H150 loop of the constant domain of the heavy chain was not visible in either structure. (Residues are labelled herein H1 to H235 for the heavy chain and L1 to L214 for the light chain and P1 to P7 for the peptides).

Along with differences in mobility of the loops mentioned above, the elbow angle in the complexed form differs from uncomplexed Fab'2F5 (142° vs. 146°). Both of these observations may be artifacts of crystal packing, since the unit cells are different, uncomplexed Fab'2F5 having a unit cell which is 30% smaller. An overlay of all Cα atoms results in an rmsd of 0.7 Å, but these shifts appear to be the result of a concerted domain movement (i.e. the change in elbow angle) rather than any modification of the antigen binding site. Superpositioning only the variable regions gives an rmsd of 0.4 Å. While the results of the structural analysis do not provide any obvious explanation for the long insertion in the V-H3 loop has been identified, its unusually hydrophobic nature for surface residues suggests it plays a role in the antibody mechanism. It may be involved in interactions with a portion of gp41 C-terminal to the epitope sequence, enhancing binding and increasing the specificity of the Fab. It may even form an integral part of the neutralization mechanism, perhaps by disrupting the conformation of the gp41 coiled-coil trimer.

Figure 2:
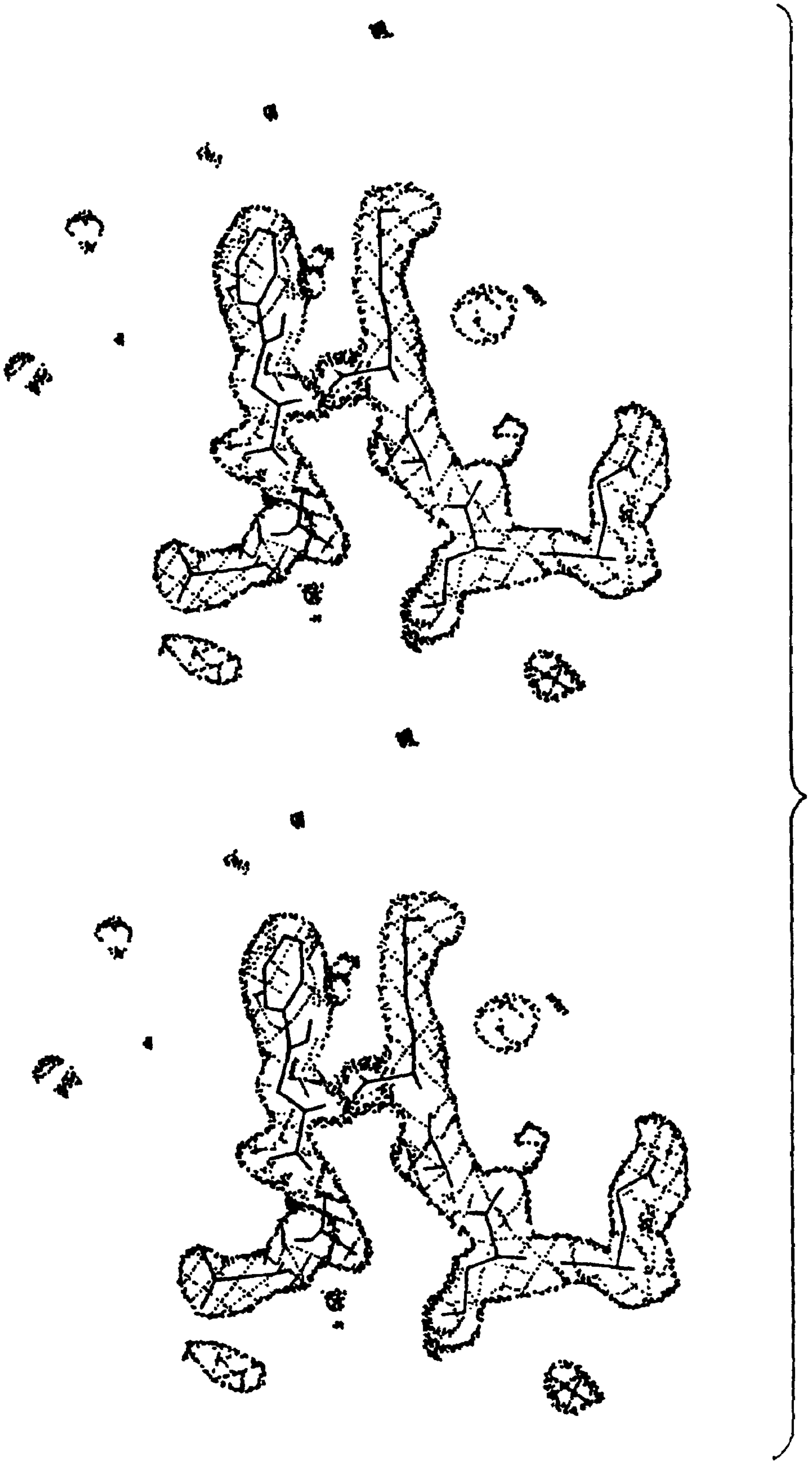
FIG. 2 is a colored stereoplot of the ELDKWAS peptide model in density, as generated by the program 0 (ref. 29). The Fo-Fc map was calculated with the peptide omitted and contoured at 3σ. A minor break in the density at P7-Ser at the contour level illustrates the slight increase in flexibility at the extremes of the bound epitope.
Figure 3:
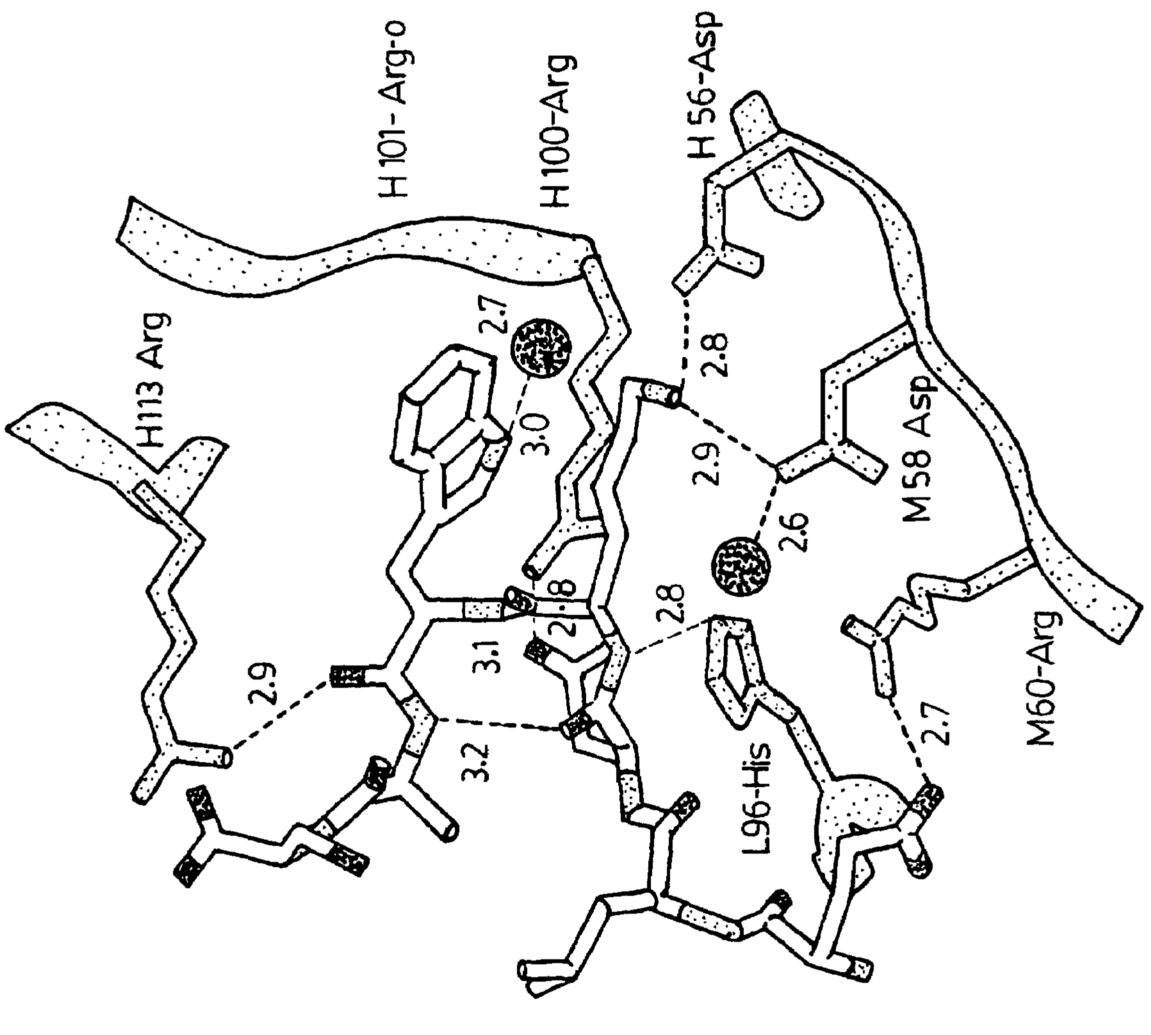
FIG. 3 is a color representation of the antigen binding site of Fab'2F5, showing protein/peptide interactions, as generated using the program SETOR (ref 30). The residues are colored by atom type: oxygen is red, nitrogen is blue, carbon is grey and sulfur is yellow. For clarity, some hydrophobic sidechains which interact with the epitope have been omitted. All bond lengths are given in Å.

In the complexed structure, the ELDKWAS (SEQ ID No: 1) peptide forms a slightly distorted, type I β turn, centered between P4-Lys and P5-Trp, (as seen in FIGS. 2 and 3), with a 3.1 Å hydrogen bond from the amide nitrogen of P6Ala to the carbonyl oxygen of P3-Asp. The arrangement is atypical in that neither position two or three in the turn is a glycine (ref. 10), but rather the bulky residues lysine and tryptophan. The dihedral angles for P5-Trp fall in the "unfavoured" region of a Ramachandran plot ($\phi=-101.7°$, $\psi=8.7°$).

Another interesting feature of the complexed structure is the stacked arrangement of the adjacent P5-Trp and P4-Lys sidechains, with hydrophobic interactions between the fully-extended alkyl chain of the P4-Lys and the aromatic rings of P5-Trp at a distance of about 3.8 Å. The lysine sidechain, whose hydrophobic methylene groups are sandwiched between P5-Trp and H54-Tyr, ends with a sharp turn at the final amino group, forming contacts with H56-Asp and H58-Asp. While the principal hydrophobic contacts of P5-Trp are the P4-Lys methylene groups, other hydrophobic residues within 4 Å of the aromatic ring system include H103-Pro and H32-Phe and the methylene groups of the sidechain of H113-Arg. A key component to the stability of the peptide configuration is the orientation of the P3-Asp sidechain, which forms strong hydrogen bonds to the backbone amide of P5-Trp as well as to L96-His-Nϵ and H100-Arg-NH1, all about 2.8 Å long. A water molecule associated with P5-Trp-Nϵ1 at 3.0 Å also forms strong hydrogen bonds to backbone carbonyls of H33-Gly and H101-Arg at 2.7 and 2.8 Å respectively. From this analysis, it can be concluded that the Asp-Lys-Trp (DKW) trio are the essential component of the protein/peptide interaction.

This conclusion is supported by mutation studies in which changes outside the DKW core do not have a dramatic effect on binding, whereas major modifications within the trio usually prevent neutralization (ref. 5). It was estimated that the LDKW (SEQ ID No.: 9) motif is 83% conserved among HIV-1 envelope glycoprotein sequence (ref. 4). For the critical portion of the epitope, DKW, conservation among 206 sequenced HIV-1 envelope proteins of all clades in the 1997 to 1998 Los Alamos HIV Sequence Database (ref. 11) is 86%. Within the B clade, conservation is 92% (91/99 sequences). Phage library screening with Mab 2F5 also selected sequences with a DRW core (ref. 4). The structure of a complex where an arginine is substituted for P4-Lys (i.e. peptide ELDRWAS (SEQ ID No: 2)) shows identical peptide conformation and contacts as the complex reported here with the consensus epitope. The total buried accessible surface area upon formation of the complex is 1025 Å (calculated as the difference in accessible surface between the intact complex and the sum of the surface areas of the peptide and uncomplexed Fab' determined using a probe of radius 1.4 Å (ref. 12)). The peptide coordinates of the complex Fab'2f5+ELDKWAS (SEQ ID No: 1) are shown in Table 4 while those for the complex Fab'2f5+ELDRWAS (SEQ ID No: 2) are shown in Table 5.

The conformation of the gp41 epitope found in the complex with Fab'2F5 and seen in detail in FIG. 3 was not anticipated. A helical conformation had been proposed (ref. 13) which was consistent with an extension of the observed coiled coil of the gp41 ectodomain (refs. 14 to 19). Most structural analyses of HIV-1 (refs. 14 to 16) or SIV (refs. 17 to 19) gp41 do not incorporate the epitope sequence, although two reports (refs. 14, 19) include a partial sequence. In one (ref. 14), ELD at the C-terminus of the crystallized portion adopted an α-helical structure, the continuation of a long (37 aa) helix. In the other, the C-terminus is an unstructured coil (ref. 19).

A conformation of the full epitope was determined as part of a fusion protein, where it was connected to the C-terminus of glutathione-S-transferase (GST) by a nine amino acid linker (ref. 20). In this environment, the epitope formed part of a series of tight turns but not the β-turn seen in the results described herein. In the GST-fusion structure, the epitope peptide interacted with a neighboring molecule in the crystal, making it probable that crystal packing forces led to the observed conformation. The gp41 peptide portion of the structure also had high thermal parameters, denoting flexibility.

Preliminary NMR studies have suggested that the ELDKWAS (SEQ ID No: 1) sequence adopts very little or no stable secondary structure. The crystal structure of Fab'2F5 elucidated herein explains the stronger immune response observed when the epitope was introduced into loops of hemagglutinin (refs. 2, 21) or recombinant antibodies (ref. 22) where a β-turn conformation might be induced, in contrast to hepatitis B virus surface antigen (ref. 8), where epitope grafting resulted in an excellent humoral response of 2F5-like binding specificity but failed to neutralize live virus, underlining the importance of the correct epitope conformation.

The conformation of the gp41 epitope set forth herein may be adopted transiently, after assembly of the mature gp41/gp120 trimers on the virus envelope, or possibly during the fusion process. A range of conformations for gp41, including the stable fusogenic form observed in the structural determinations made herein, as well as an intermediate "unsprung" and non-fusogenic form has been proposed by several investigators (refs. 14, 23). A short life span of the antigen would be consistent with its low immunogenicity and the consequent absence of Mab 2F5 in the antisera of most infected patients. As well, passive immunization with Mab 2F5 in chimpanzees failed to neutralize HIV-1, resulting in delayed infection and lower viral loads, but not protection (ref. 6). This result was presumably due to insufficient opportunity for antibody binding, either because of low antibody concentration or the short lifetime of the antigenic conformation. As the only identified cross-neutralizing antibody against gp41, Mab 2F5 is an important focus in HIV-1 vaccine research. It is one of only three broadly neutralizing monoclonal antibodies identified to date and the only one with a short, continuous epitope. The other two known cross-neutralizing Mab's are b12 and 2G12 which define epitopes at the CD4 binding site and V3/V4 loops of gp120 respectively (ref. 6), but in these cases the epitopes are discontinuous and involve both peptide and carbohydrate interactions (refs. 5, 6).

Development of a peptide-mimetic constrained to adopt the conformation of the gp41 sequence found in the structure of Fab'2F5 could overcome the low immunogenicity of the epitope, making such a compound a useful component of a future HIV-1 vaccine.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, peptide-mimetics chemistry, protein biochemistry, crystallography and immunology used but not explicitly described in this disclosure and these Examples are amply reported in the scientific literature and are well within the ability of those skilled in the art.

Example 1

This Example shows the preparation, purification and crystallization of Fab'2F5 and its epitope complex.

Intact human IAM 2F5 IgG antibody was transformed into $F(ab')_2$ using standard pepsin protocols. $F(ab')_2$ was then stored with 1% (w/v) clinical human albumin added to the solution for stability. To separate the protein from the albumin, DE52 cellulose was swollen in 20 mM Tris pH 8.0 and packed into a column 3 cm wide, 5 cm high, providing about 30 mL bed volume. The column was washed overnight with 2 L of 20 mM Tris pH 8.0.

55 ml protein at 1.1 mg/ml concentration were dialysed against 2×4 to 5 L of 20 mM Tris pH 8.0 and the conductivity and pH of the buffer, flow through and protein concentration were checked to ensure the protein bound to the column. The protein was loaded onto the column by pumping on at 1 to 5 mL/min, with albumen binding to the column while the F(ab')2 does not. Buffer A (20 mM Tris pH 8.0) was run through the column until the $OD_{280}$ went down to baseline and approximately 7 mL fractions were collected.

The albumin was eluted with a salt gradient of 20 mM Tris pH 8.0, 20 mM Tris pH 8.0+0.2 M NaCl, to ensure no other proteins were present. The flow-through protein was concentrated, producing 5×500 μL of $F(ab')_2$ at 23 mg/ml. The sample was confirmed to be $F(ab')_2$ by reducing and non-reducing native and SDS-PAGE gels as well as by a positive antigen-catch ELISA assay targetting the k-chain followed by a negative assay targetting the Fc part of a human antibody molecule.

200 μl of Fab' at 23 mg/mL were diluted to 4 mL with 0.1 M Tris pH 8.0. 400 μL 100 mM DTT in 0.1 M Tris pH 8.0 were added to the 4 mL to provide a final concentration of 10 mM in DTT. The solution was incubated at room temperature for an hour, 30 μL of a 500 mM iodoacetamide solution in 0.1 M Tris pH 8.0 were added and the solution left for a further 30 minutes. The Fab' was dialyzed overnight against 20 mM Tris pH 8.0 and concentrated to 10 mg/mL for use in crystallization setups.

Crystals of uncomplexed Fab' grew from hanging drops of 5 mg/mL protein with 1.0 M ammonium sulfate at pH 5.8 as precipitant and grew as needles. Complexes were co-crystallized by adding a 3:1 ratio of peptide ELDKWAS (SEQ ID No: 1) to protein and incubating overnight before setting up as hanging drops of 5 mg/mL complex at pH 5.8, using 1.6 M ammonium sulfate at pH 7.0 as precipitant. The crystals grew in two days as large square bipyramids.

The sequence of the heavy and light variable domains has recently been published (ref. 10) and agrees with the one used in this study with a single correction at amino acid H110, which is a serine rather than a proline as originally stated. The full amino acid sequences of the variable and constant domains of the Fab' fragment are shown in Table 1 below (SEQ ID Nos: 6 and 7).

Crystals of the free Fab' belong to the space group $P2_12_12_1$ (unit cell: a=63.6 Å; b=76.4 Å; c=94.7 Å) and grow as needles. Crystals of the complex also adopt space group $P2_12_12_1$ (unit cell: a=59.0 Å; b=65.0 Å; c=175.6 Å) and grow as square bipyramids. Crystals were flash frozen for data collection. Data were collected on a Rigaku FR-C equipped with Molecular Structure Corp mirror optics and with a Mar345 image plate detector (Fab'2F5 ) and at the National Synchrotron Light Source in Brookhaven using a Mar30 detector (complex). Data were processed using DENZO and SCALEPACK (HKL Research).

Example 2

This Example describes the solution of the structure of the Fab'2F5 complexed and uncomplexed.

The structure of the Fab'2F5 complex was solved by molecular replacement (ref. 24) using PDB entry ICLZ (ref. 25) minus sidechains and hypervariable loops as the search model. Constant and variable regions were used as independent models. The correct solution had a correlation coefficient of 35.3 (R=47.3%) using data to 3.3 Å. The CNS package (ref. 26) was used for refinement. A $2F_o$-$F_c$ map generated after rigid body refinement of the polyalanine model allowed placement of most sidechains. After a cycle of simulated annealing, the hypervariable loops were included. Density for the peptide was clear at this point and could be fitted unambiguously. Following another cycle of annealing, positional and B-factor refinement, waters were included where peaks of >3.5 were found in a difference map at an appropriate distance from a donor or acceptor atom.

The structure of the uncomplexed Fab'2F5 was solved by molecular replacement using the refined Fab'2F5 complex minus peptide as the search model. Correlation coefficient was 53.7, R=39.0%. Refinement followed the same procedure as for the complex. Statistics of data collection, processing and structure refinement are given in Table 2 below. The coordinates of the crystal structures have been deposited on Apr. 9, 1999 in the Brookhaven Protein Data Bank under Accession Nos. 2F5A for the uncomplexed structure and 2F5B for the Fab'2F5 -epitope complex.

Example 3

This Example demonstrates the utility of the three-dimensional structural information of Katinger's epitope (Examples 1 and 2) in the rational design of constraint peptide-based vaccines.

(SEQ ID No: 3)

1. ECDKWCS CLP-634

Based on the structural information, the Katinger's epitope may be locked with a disulfide bridge between positions 2 and 6 in the peptide ECDKWCS (CLP-634) (SEQ ID No: 3).

The linear peptide ECDKWCS was synthesised manually, on PAM support, by using a standard Solid Phase Peptide Synthesis methodology, with a t-Boc strategy. The crude peptide was cleaved off the resin by high-HF procedure. The crude material (54 mg) was dissolved in methanol (500 mL). 50 mM iodine in methanol was added dropwise, with stirring, until solution became pale-yellow. After 1 min of stirring, Dowex IX2-200 (acetate) resin (approx. 9 g) was added. The stirring was continued until solution became colourless. The resin was filtered off, 50 ml of water was added, the mixture was concentrated in vacuo, frozen and lyophilised. The crude cyclic peptide was purified by RP-HPLC.

2. EdapDKWES CLP-1309 (SEQ ID No: 4)

Based on the structural information, the Katinger's peptide also may be constrained with a lactam bond between positions 2 and 6 in the peptide EDapDKWES (CLP-1309) (SEQ ID No: 4).

The peptide: t-Boc-Glu(OBzl)-Dap(Fmoc)-Asp(OBzl)-Lys(2Cl-Cbz)-Trp(For)-Glu(OFm)-Ser(Bzl)-RESIN was assembled on a PAM solid support. Sidechains of Dap(2) and Glu(6) were subsequently deprotected by treatment with 25% piperidine. The sidechain cyclization was performed on the resin by adding four equivalents of HBTU and 8 equivalents of DIEA and shaking the mixture overnight. The cyclic peptide was cleaved off the resin by a standard HF procedure and the crude product was purified by RP-HPLC.

Abbreviations used in this Example are:
Dap=diaminopropionic acid
HBTU=O-Benzotriazolyl-N,N,N',N'-tetramethyluronium Hexafluorophosphate
DIEA=Di-isopropylethylamine
PAM=4-Hydroxymethyl-phenylacetamidomethyl resin
Bzl=Benzyl
2-Cl-Cbz=2-Chlorobenzyloxycarbonyl
For=Formyl
t-Boc=t-Butloxycarbonyl
Fmoc=Fluorenylmethoxycarbonyl
Fm=Fluorenylmethyl Both peptides CLP-634 and CLP-1309 were found to be capable of forming an immuno-complex with monoclonal antibody 2F5 and were subsequently co-crystallized with the Fab' fragment. These results indicated that the constrained peptides may mimic the Katinger's epitope and would be useful as peptide-based vaccines.

Example 4

This Example demonstrates the formation of constrained peptide-carrier conjugates, for use as anti-HIV vaccines.

In order to conjugate the constrained peptide CLP-1309 (Example 3) to a carrier protein, a tetra-peptide Cys-Gly-Gly-Gly (SEQ ID No.: 10) was linked to CLP-1309 at the N-terminal end and the resultant peptide was named as CLP-1491. Similarly, a tetra-peptide Gly-Gly-Gly-Cys (SEQ ID No.: 11) was linked to CLP-1309 at the C-terminal end, and so the resultant peptide was named as CLP-1492.

Fifty microlitre of m-maleimidobenzoyl-N-hydroxysuccinimide (MBS, Pierce, 2 mg; 6.3 mmol in 1 mL of tetrahydrofuran or methanol) was added to a protein solution (approximately 10 mg of Hin47 or tetanus toxoid in 2 mL of 0.1 M phosphate buffer, pH 7.5). The reaction mixture was stirred for 30 min at room temperature under argon. The reaction mixture was applied to a Sephadex G-25 column (20×300 mm) equilibrated with 20 mM ammonium bicarbonate buffer, pH 7.2 and eluted with the same buffer. Elution was monitored by absorbance at 230 nm, and the eluted protein peak was pooled. The number of maleimide groups incorporated into the carrier was determined by adding excess 2-mercaptoethanol to the activated carrier-MBS and back-titrating the excess using a modified Eliman's method (ref. 31).

A general protocol for peptide-carrier conjugates has been described (ref. 32). Briefly, synthetic peptide (1 mg/mL) in degassed PBS buffer, pH 7.5 mixed with carrier-MBS (1 mg/mL). The reaction mixture was stirred overnight at room temperature under argon atmosphere. Excess N-ethyl-maleimide (Aldrich) was added to quench the reaction, and stirring continued for an additional hour. The insoluble precipitate was filtered off, and the filtrate was subjected to gel filtration chromatography using a Sephadex G-25 column. The peptide-carrier conjugate was collected. The molar ratio of carrier to peptide was determined by using amino acid analysis.

SUMMARY OF DISCLOSURE

In summary of this disclosure, the crystal structure of the Fab'2F5 fragment has been elucidated, both in uncomplexed form and complexed with the epitope ELDKWAS (SEQ ID No: 1), and peptides synthesized to correspond to the constrained structure of the peptide-protein interactions. Modifications are possible within the scope of this invention.

TABLE 1

ALQLTQSPSS LSASVGDRIT ITCRASQGVT SALAWYRQKP GSPPQLLIYD ASSLESGVPS
RFSGSGSGTE FTLTISTLRP EDFATYYCQQ LHFYPRTFGG GTRVDVRRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC (SEQ ID No.: 6)
RITLKESGPP LVKPTQTLTL TCSFSGFSLS DFGVGVGWIR QPPGKALEWL AIIYSDDDKR
YSPSLNTRLT ITKDTSKNQV VLVMTRVSPV DTATYFCAHR RGPTTLFGVP IARGPVNAMD
VWGQGITVTI SSASTKGPSV FPLAPSSKST SGGTAALGCL VKDYFPEPVT VSWNSGALTS
GVHTFPAVLQ SSGLYSLSSV VTVPSSSLGT QTYICNVNHK PSNTKVDKKV EPKSCDKTHT
CPPCPAPELL GGPSVFLFPP KPKDTLMISR TPEVTCVVVD VSHEDPEVKF NWYVDGVEVH
NAKTKPREEQ YNSTYRVVSV LTVLHQDWLN GKEYKCKVSN KAFPAPIEKT ISKAKGQPRE
PQVYTLPPSR DELTKNQVSL TCLVKGFYPS DIAVEWESNG QPENNYKTTP PVLDSDGSFF
LYSKLTVDKS RWQQGNVFSC SVMHEALHNH YTQKSLSLSP GK (SEQ ID No.: 7)

TABLE 2

| Data Collection, Processing and Structure Refinement Parameters | | |
|---|---|---|
| Compound | Fab'2F5 | Fab'2F5-ELDKWAS |
| Crystal system; space group | orthorhombic; $P2_12_12_1$ | orthorhombic; $P2_12_12_1$ |
| Unit cell (Å) | a = 63.3 | a = 58.0; |
| | b = 76.3 | b = 65.0, |
| | c = 94.4 | c = 175.6 |
| Resolution range (Å) | 20.0-2.05 | 12.0-2.0 |
| # of reflections | 89376 | 118126 |
| # unique reflections | 28045 | 41062 |

TABLE 2-continued

| Data Collection, Processing and Structure Refinement Parameters | | |
|---|---|---|
| Completeness; completeness top bin (%) | 92; 93 | 90; 92 |
| $R_{sym}$; $R_{sym}$ top bin (%) | 7.0; 31.3 | 3.5; 16.6 |
| -cutoff | 0.0 | 1.0 |
| % data in test set | 5 | 5 |
| # water molecules in model | 268 | 357 |
| R, $R_{free}$ | 0.23, 0.27 | 0.22, 0.25 |
| Rmsd bonds (Å); angles (°) | 0.007; 1.4 | 0.010; 1.5 |

TABLE 3

| | | | | | | | | | | |
|---|---|---|---|---|---|---|---|---|---|---|
| ATOM | 2399 | N | ALA H | 98 | −.049 | 39.377 | 79.646 | 1.00 | 21.77 | H |
| ATOM | 2400 | CA | ALA H | 98 | 1.135 | 39.444 | 80.483 | 1.00 | 21.70 | H |
| ATOM | 2401 | CB | ALA H | 98 | 2.361 | 39.794 | 79.633 | 1.00 | 21.47 | H |
| ATOM | 2402 | C | ALA H | 98 | .979 | 40.460 | 81.598 | 1.00 | 21.53 | H |
| ATOM | 2403 | O | ALA H | 98 | .223 | 41.419 | 81.490 | 1.00 | 21.06 | H |
| ATOM | 2404 | N | HIS H | 99 | 1.731 | 40.229 | 82.660 | 1.00 | 21.37 | H |
| ATOM | 2405 | CA | HIS H | 99 | 1.719 | 41.072 | 83.841 | 1.00 | 21.17 | H |
| ATOM | 2406 | CB | HIS H | 99 | 1.956 | 40.169 | 85.059 | 1.00 | 21.35 | H |
| ATOM | 2407 | CG | HIS H | 99 | 2.229 | 40.897 | 86.336 | 1.00 | 21.04 | H |
| ATOM | 2408 | CD2 | HIS H | 99 | 1.395 | 41.316 | 87.319 | 1.00 | 20.90 | H |
| ATOM | 2409 | ND1 | HIS H | 99 | 3.504 | 41.224 | 86.746 | 1.00 | 21.12 | H |
| ATOM | 2410 | CE1 | HIS H | 99 | 3.446 | 41.808 | 87.931 | 1.00 | 20.64 | H |
| ATOM | 2411 | NE2 | HIS H | 99 | 2.179 | 41.876 | 88.301 | 1.00 | 20.95 | H |
| ATOM | 2412 | C | HIS H | 99 | 2.748 | 42.194 | 83.773 | 1.00 | 21.64 | H |
| ATOM | 2413 | O | HIS H | 99 | 3.831 | 42.026 | 83.207 | 1.00 | 21.32 | H |
| ATOM | 2414 | N | ARG H | 100 | 2.379 | 43.355 | 84.306 | 1.00 | 21.79 | H |
| ATOM | 2415 | CA | ARG H | 100 | 3.292 | 44.483 | 84.354 | 1.00 | 22.26 | H |
| ATOM | 2416 | CB | ARG H | 100 | 2.824 | 45.673 | 83.507 | 1.00 | 22.31 | H |
| ATOM | 2417 | CG | ARG H | 100 | 3.884 | 46.772 | 83.478 | 1.00 | 22.62 | H |
| ATOM | 2418 | CD | ARG H | 100 | 3.486 | 48.026 | 82.712 | 1.00 | 22.45 | H |
| ATOM | 2419 | NE | ARG H | 100 | 4.626 | 48.941 | 82.623 | 1.00 | 22.59 | H |
| ATOM | 2420 | CZ | ARG H | 100 | 4.569 | 50.179 | 82.133 | 1.00 | 22.62 | H |
| ATOM | 2421 | NH1 | ARG H | 100 | 3.425 | 50.676 | 81.684 | 1.00 | 22.75 | H |
| ATOM | 2422 | NH2 | ARG H | 100 | 5.674 | 50.910 | 82.055 | 1.00 | 23.15 | H |
| ATOM | 2423 | C | ARG H | 100 | 3.363 | 44.906 | 85.805 | 1.00 | 22.74 | H |
| ATOM | 2424 | O | ARG H | 100 | 2.337 | 45.128 | 86.460 | 1.00 | 22.03 | H |
| ATOM | 2425 | N | ARG H | 101 | 4.579 | 45.001 | 86.304 | 1.00 | 23.46 | H |
| ATOM | 2426 | CA | ARG H | 101 | 4.809 | 45.388 | 87.678 | 1.00 | 24.42 | H |
| ATOM | 2427 | CB | ARG H | 101 | 6.287 | 45.169 | 88.017 | 1.00 | 25.61 | H |
| ATOM | 2428 | CG | ARG H | 101 | 6.557 | 44.099 | 89.047 | 1.00 | 27.15 | H |
| ATOM | 2429 | CD | ARG H | 101 | 7.573 | 43.067 | 88.572 | 1.00 | 28.68 | H |
| ATOM | 2430 | NE | ARG H | 101 | 8.851 | 43.615 | 88.118 | 1.00 | 29.23 | H |
| ATOM | 2431 | CZ | ARG H | 101 | 9.867 | 42.858 | 87.697 | 1.00 | 29.78 | H |
| ATOM | 2432 | NH1 | ARG H | 101 | 9.747 | 41.535 | 87.681 | 1.00 | 30.18 | H |
| ATOM | 2433 | NH2 | ARG H | 101 | 11.001 | 43.410 | 87.276 | 1.00 | 29.91 | H |
| ATOM | 2434 | C | ARG H | 101 | 4.448 | 46.846 | 87.902 | 1.00 | 24.54 | H |
| ATOM | 2435 | O | ARG H | 101 | 4.544 | 47.668 | 86.996 | 1.00 | 23.94 | H |
| ATOM | 2436 | N | GLY H | 102 | 4.014 | 47.156 | 89.118 | 1.00 | 25.02 | H |
| ATOM | 2437 | CA | GLY H | 102 | 3.709 | 48.529 | 89.453 | 1.00 | 26.02 | H |
| ATOM | 2438 | C | GLY H | 102 | 4.957 | 49.055 | 90.136 | 1.00 | 27.10 | H |
| ATOM | 2439 | O | GLY H | 102 | 5.889 | 48.280 | 90.375 | 1.00 | 26.58 | H |
| ATOM | 2440 | N | PRO H | 103 | 5.031 | 50.357 | 90.449 | 1.00 | 27.97 | H |
| ATOM | 2441 | CD | PRO H | 103 | 4.057 | 51.435 | 90.215 | 1.00 | 28.46 | H |
| ATOM | 2442 | CA | PRO H | 103 | 6.218 | 50.901 | 91.111 | 1.00 | 29.02 | H |
| ATOM | 2443 | CB | PRO H | 103 | 5.863 | 52.379 | 91.269 | 1.00 | 28.75 | H |
| ATOM | 2444 | CG | PRO H | 103 | 4.982 | 52.630 | 90.056 | 1.00 | 28.56 | H |
| ATOM | 2445 | C | PRO H | 103 | 6.458 | 50.226 | 92.457 | 1.00 | 30.21 | H |
| ATOM | 2446 | O | PRO H | 103 | 5.515 | 49.927 | 93.185 | 1.00 | 30.26 | H |
| ATOM | 2447 | N | THR H | 104 | 7.723 | 49.967 | 92.772 | 1.00 | 31.28 | H |
| ATOM | 2448 | CA | THR H | 104 | 8.073 | 49.360 | 94.048 | 1.00 | 32.89 | H |
| ATOM | 2449 | CB | THR H | 104 | 9.586 | 49.042 | 94.115 | 1.00 | 32.77 | H |
| ATOM | 2450 | OG1 | THR H | 104 | 9.898 | 48.014 | 93.167 | 1.00 | 33.00 | H |
| ATOM | 2451 | CG2 | THR H | 104 | 9.987 | 48.579 | 95.514 | 1.00 | 32.60 | H |
| ATOM | 2452 | C | THR H | 104 | 7.720 | 50.366 | 95.141 | 1.00 | 33.71 | H |
| ATOM | 2453 | O | THR H | 104 | 7.978 | 51.559 | 94.994 | 1.00 | 33.67 | H |

TABLE 3-continued

| | | | | | | | | | | |
|---|---|---|---|---|---|---|---|---|---|---|
| ATOM | 2454 | N | THR H | 105 | 7.123 | 49.889 | 96.225 | 1.00 | 35.02 | H |
| ATOM | 2455 | CA | THR H | 105 | 6.745 | 50.769 | 97.321 | 1.00 | 36.43 | H |
| ATOM | 2456 | CB | THR H | 105 | 5.217 | 50.723 | 97.589 | 1.00 | 36.53 | H |
| ATOM | 2457 | OG1 | THR H | 105 | 4.837 | 49.399 | 97.990 | 1.00 | 36.95 | H |
| ATOM | 2458 | CG2 | THR H | 105 | 4.437 | 51.116 | 96.334 | 1.00 | 36.64 | H |
| ATOM | 2459 | C | THR H | 105 | 7.470 | 50.384 | 98.609 | 1.00 | 37.35 | H |
| ATOM | 2460 | O | THR H | 105 | 7.892 | 49.242 | 98.773 | 1.00 | 37.48 | H |
| ATOM | 2461 | N | LEU H | 106 | 7.625 | 51.354 | 99.506 | 1.00 | 38.42 | H |
| ATOM | 2462 | CA | LEU H | 106 | 8.264 | 51.132 | 100.804 | 1.00 | 39.62 | H |
| ATOM | 2463 | CB | LEU H | 106 | 9.633 | 51.813 | 100.877 | 1.00 | 39.53 | H |
| ATOM | 2464 | CG | LEU H | 106 | 10.385 | 51.596 | 102.199 | 1.00 | 39.63 | H |
| ATOM | 2465 | CD1 | LEU H | 106 | 10.643 | 50.107 | 102.396 | 1.00 | 39.65 | H |
| ATOM | 2466 | CD2 | LEU H | 106 | 11.694 | 52.362 | 102.193 | 1.00 | 39.35 | H |
| ATOM | 2467 | C | LEU H | 106 | 7.319 | 51.756 | 101.825 | 1.00 | 40.38 | H |
| ATOM | 2468 | O | LEU H | 106 | 7.113 | 52.973 | 101.828 | 1.00 | 40.43 | H |
| ATOM | 2469 | N | PHE H | 107 | 6.753 | 50.916 | 102.687 | 1.00 | 41.38 | H |
| ATOM | 2470 | CA | PHE H | 107 | 5.784 | 51.366 | 103.679 | 1.00 | 42.27 | H |
| ATOM | 2471 | CB | PHE H | 107 | 6.443 | 52.208 | 104.774 | 1.00 | 43.05 | H |
| ATOM | 2472 | CG | PHE H | 107 | 7.522 | 51.488 | 105.525 | 1.00 | 43.75 | H |
| ATOM | 2473 | CD1 | PHE H | 107 | 8.855 | 51.624 | 105.255 | 1.00 | 44.10 | H |
| ATOM | 2474 | CD2 | PHE H | 107 | 7.202 | 50.645 | 106.585 | 1.00 | 44.17 | H |
| ATOM | 2475 | CE1 | PHE H | 107 | 9.857 | 50.935 | 105.829 | 1.00 | 44.32 | H |
| ATOM | 2476 | CE2 | PHE H | 107 | 8.195 | 49.948 | 107.265 | 1.00 | 44.42 | H |
| ATOM | 2477 | CZ | PHE H | 107 | 9.527 | 50.094 | 106.887 | 1.00 | 44.38 | H |
| ATOM | 2478 | C | PHE H | 107 | 4.736 | 52.194 | 102.946 | 1.00 | 42.37 | H |
| ATOM | 2479 | O | PHE H | 107 | 4.355 | 53.276 | 103.390 | 1.00 | 42.68 | H |
| ATOM | 2480 | N | GLY H | 108 | 4.298 | 51.681 | 101.799 | 1.00 | 42.27 | H |
| ATOM | 2481 | CA | GLY H | 108 | 3.290 | 52.368 | 101.015 | 1.00 | 42.09 | H |
| ATOM | 2482 | C | GLY H | 108 | 3.777 | 53.434 | 100.051 | 1.00 | 41.71 | H |
| ATOM | 2483 | O | GLY H | 108 | 3.065 | 53.782 | 99.112 | 1.00 | 42.19 | H |
| ATOM | 2484 | N | VAL H | 109 | 4.979 | 53.957 | 100.260 | 1.00 | 40.92 | H |
| ATOM | 2485 | CA | VAL H | 109 | 5.491 | 54.996 | 99.373 | 1.00 | 40.10 | H |
| ATOM | 2486 | CB | VAL H | 109 | 6.406 | 55.988 | 100.138 | 1.00 | 40.30 | H |
| ATOM | 2487 | CG1 | VAL H | 109 | 6.868 | 57.097 | 99.209 | 1.00 | 40.21 | H |
| ATOM | 2488 | CG2 | VAL H | 109 | 5.667 | 56.568 | 101.330 | 1.00 | 40.54 | H |
| ATOM | 2489 | C | VAL H | 109 | 6.275 | 54.441 | 98.184 | 1.00 | 39.35 | H |
| ATOM | 2490 | O | VAL H | 109 | 7.226 | 53.678 | 98.353 | 1.00 | 39.16 | H |
| ATOM | 2491 | N | PRO H | 110 | 5.867 | 54.805 | 96.956 | 1.00 | 38.61 | H |
| ATOM | 2492 | CD | PRO H | 110 | 4.728 | 55.654 | 96.569 | 1.00 | 38.51 | H |
| ATOM | 2493 | CA | PRO H | 110 | 6.567 | 54.329 | 95.757 | 1.00 | 37.67 | H |
| ATOM | 2494 | CB | PRO H | 110 | 5.728 | 54.922 | 94.629 | 1.00 | 37.96 | H |
| ATOM | 2495 | CG | PRO H | 110 | 5.221 | 56.214 | 95.258 | 1.00 | 38.42 | H |
| ATOM | 2496 | C | PRO H | 110 | 7.988 | 54.887 | 95.782 | 1.00 | 36.69 | H |
| ATOM | 2497 | O | PRO H | 110 | 8.179 | 56.099 | 95.921 | 1.00 | 36.53 | H |
| ATOM | 2498 | N | ILE H | 111 | 8.977 | 54.006 | 95.654 | 1.00 | 35.32 | H |
| ATOM | 2499 | CA | ILE H | 111 | 10.377 | 54.419 | 95.692 | 1.00 | 34.04 | H |
| ATOM | 2500 | CB | ILE H | 111 | 11.087 | 53.834 | 96.927 | 1.00 | 34.06 | H |
| ATOM | 2501 | CG2 | ILE H | 111 | 10.441 | 54.361 | 98.204 | 1.00 | 34.21 | H |
| ATOM | 2502 | CG1 | ILE H | 111 | 11.017 | 52.305 | 96.876 | 1.00 | 34.03 | H |
| ATOM | 2503 | CD1 | ILE H | 111 | 11.776 | 51.607 | 97.990 | 1.00 | 33.88 | H |
| ATOM | 2504 | C | ILE H | 111 | 11.180 | 54.009 | 94.463 | 1.00 | 33.02 | H |
| ATOM | 2505 | O | ILE H | 111 | 12.367 | 54.322 | 94.365 | 1.00 | 32.88 | H |
| ATOM | 2506 | N | ALA H | 112 | 10.551 | 53.296 | 93.536 | 1.00 | 31.78 | H |
| ATOM | 2507 | CA | ALA H | 112 | 11.255 | 52.862 | 92.338 | 1.00 | 30.94 | H |
| ATOM | 2508 | CB | ALA H | 112 | 12.149 | 51.670 | 92.667 | 1.00 | 30.98 | H |
| ATOM | 2509 | C | ALA H | 112 | 10.300 | 52.496 | 91.213 | 1.00 | 30.17 | H |
| ATOM | 2510 | O | ALA H | 112 | 9.394 | 51.681 | 91.398 | 1.00 | 30.19 | H |
| ATOM | 2511 | N | ARG H | 113 | 10.506 | 53.091 | 90.046 | 1.00 | 29.21 | H |
| ATOM | 2512 | CA | ARG H | 113 | 9.651 | 52.797 | 88.905 | 1.00 | 28.40 | H |
| ATOM | 2513 | CB | ARG H | 113 | 9.199 | 54.100 | 88.239 | 1.00 | 28.78 | H |
| ATOM | 2514 | CG | ARG H | 113 | 10.337 | 55.009 | 87.853 | 1.00 | 28.97 | H |
| ATOM | 2515 | CD | ARG H | 113 | 9.850 | 56.258 | 87.132 | 1.00 | 29.05 | H |
| ATOM | 2516 | NE | ARG H | 113 | 10.971 | 57.131 | 86.821 | 1.00 | 29.19 | H |
| ATOM | 2517 | CZ | ARG H | 113 | 10.940 | 58.104 | 85.916 | 1.00 | 29.34 | H |
| ATOM | 2518 | NH1 | ARG H | 113 | 9.831 | 58.339 | 85.217 | 1.00 | 28.91 | H |
| ATOM | 2519 | NH2 | ARG H | 113 | 12.029 | 58.835 | 85.702 | 1.00 | 29.08 | H |
| ATOM | 2520 | C | ARG H | 113 | 10.353 | 51.901 | 87.892 | 1.00 | 27.85 | H |
| ATOM | 2521 | O | ARG H | 113 | 9.746 | 51.462 | 86.920 | 1.00 | 27.45 | H |
| ATOM | 2522 | N | GLY H | 114 | 11.632 | 51.620 | 88.122 | 1.00 | 27.08 | H |
| ATOM | 2523 | CA | GLY H | 114 | 12.367 | 50.768 | 87.203 | 1.00 | 26.56 | H |
| ATOM | 2524 | C | GLY H | 114 | 11.655 | 49.456 | 86.897 | 1.00 | 26.06 | H |
| ATOM | 2525 | O | GLY H | 114 | 11.588 | 49.036 | 85.738 | 1.00 | 25.97 | H |
| ATOM | 2526 | N | PRO H | 115 | 11.132 | 48.763 | 87.918 | 1.00 | 25.66 | H |
| ATOM | 2527 | CD | PRO H | 115 | 11.212 | 49.041 | 89.362 | 1.00 | 25.99 | H |
| ATOM | 2528 | CA | PRO H | 115 | 10.432 | 47.497 | 87.700 | 1.00 | 25.02 | H |
| ATOM | 2529 | CB | PRO H | 115 | 10.028 | 47.087 | 89.119 | 1.00 | 25.85 | H |
| ATOM | 2530 | CG | PRO H | 115 | 9.921 | 48.435 | 89.838 | 1.00 | 26.45 | H |
| ATOM | 2531 | C | PRO H | 115 | 9.239 | 47.534 | 86.734 | 1.00 | 24.10 | H |
| ATOM | 2532 | O | PRO H | 115 | 8.808 | 46.495 | 86.252 | 1.00 | 23.75 | H |

TABLE 3-continued

| | | | | | | | | | | |
|---|---|---|---|---|---|---|---|---|---|---|
| ATOM | 2533 | N | VAL H | 116 | 8.700 | 48.710 | 86.446 | 1.00 | 22.92 | H |
| ATOM | 2534 | CA | VAL H | 116 | 7.565 | 48.764 | 85.531 | 1.00 | 22.26 | H |
| ATOM | 2535 | CB | VAL H | 116 | 6.730 | 50.062 | 85.719 | 1.00 | 21.84 | H |
| ATOM | 2536 | CG1 | VAL H | 116 | 6.401 | 50.266 | 87.199 | 1.00 | 21.48 | H |
| ATOM | 2537 | CG2 | VAL H | 116 | 7.472 | 51.255 | 85.150 | 1.00 | 20.99 | H |
| ATOM | 2538 | C | VAL H | 116 | 8.022 | 48.696 | 84.066 | 1.00 | 22.08 | H |
| ATOM | 2539 | O | VAL H | 116 | 7.198 | 48.513 | 83.166 | 1.00 | 22.38 | H |
| ATOM | 2540 | N | AEN H | 117 | 9.327 | 48.824 | 83.826 | 1.00 | 21.63 | H |
| ATOM | 2541 | CA | ASN H | 117 | 9.826 | 48.813 | 82.455 | 1.00 | 21.64 | H |
| ATOM | 2542 | CB | ASN H | 117 | 11.071 | 49.697 | 82.338 | 1.00 | 21.90 | H |
| ATOM | 2543 | CG | ASN H | 117 | 10.748 | 51.173 | 82.526 | 1.00 | 22.54 | H |
| ATOM | 2544 | OD1 | ASN H | 117 | 9.686 | 51.630 | 82.116 | 1.00 | 22.65 | H |
| ATOM | 2545 | ND2 | ASN H | 117 | 11.673 | 51.922 | 83.115 | 1.00 | 22.26 | H |
| ATOM | 2546 | C | ASN H | 117 | 10.070 | 47.451 | 81.814 | 1.00 | 21.39 | H |
| ATOM | 2547 | O | ASN H | 117 | 11.186 | 47.122 | 81.396 | 1.00 | 21.27 | H |
| ATOM | 2548 | N | ALA H | 118 | 8.984 | 46.691 | 81.716 | 1.00 | 21.30 | H |
| ATOM | 2549 | CA | ALA H | 118 | 8.964 | 45.364 | 81.123 | 1.00 | 21.19 | H |
| ATOM | 2550 | CB | ALA H | 118 | 10.093 | 44.511 | 81.695 | 1.00 | 21.58 | H |
| ATOM | 2551 | C | ALA H | 118 | 7.632 | 44.713 | 81.466 | 1.00 | 21.25 | H |
| ATOM | 2552 | O | ALA H | 118 | 6.898 | 45.197 | 82.333 | 1.00 | 21.59 | H |
| ATOM | 2553 | N | MET H | 119 | 7.329 | 43.630 | 80.759 | 1.00 | 21.14 | H |
| ATOM | 2554 | CA | MET H | 119 | 6.153 | 42.814 | 81.012 | 1.00 | 21.00 | H |
| ATOM | 2555 | CB | MET H | 119 | 5.413 | 42.486 | 79.712 | 1.00 | 21.35 | H |
| ATOM | 2556 | CG | MET H | 119 | 4.782 | 43.691 | 79.004 | 1.00 | 21.59 | H |
| ATOM | 2557 | SD | MET H | 119 | 3.738 | 44.767 | 80.053 | 1.00 | 22.00 | H |
| ATOM | 2558 | CE | MET H | 119 | 4.880 | 45.836 | 80.681 | 1.00 | 24.35 | H |
| ATOM | 2559 | C | MET H | 119 | 6.907 | 41.594 | 81.542 | 1.00 | 21.33 | H |
| ATOM | 2560 | O | MET H | 119 | 7.499 | 40.829 | 80.773 | 1.00 | 21.24 | H |
| ATOM | 2561 | N | ASP H | 120 | 6.894 | 41.430 | 82.858 | 1.00 | 21.43 | H |
| ATOM | 2562 | CA | ASP H | 120 | 7.679 | 40.381 | 83.500 | 1.00 | 21.62 | H |
| ATOM | 2563 | CB | ASP H | 120 | 8.014 | 40.819 | 84.932 | 1.00 | 21.73 | H |
| ATOM | 2564 | CG | ASP H | 120 | 6.806 | 40.826 | 85.840 | 1.00 | 22.35 | H |
| ATOM | 2565 | OD1 | ASP H | 120 | 5.661 | 40.878 | 85.330 | 1.00 | 21.92 | H |
| ATOM | 2566 | OD2 | ASP H | 120 | 7.011 | 40.807 | 87.075 | 1.00 | 21.94 | H |
| ATOM | 2567 | C | ASP H | 120 | 7.209 | 38.931 | 83.499 | 1.00 | 21.67 | H |
| ATOM | 2568 | O | ASP H | 120 | 8.020 | 38.027 | 83.688 | 1.00 | 21.12 | H |

TABLE 4

ELDKWAS:

| | | | | | | | | | | |
|---|---|---|---|---|---|---|---|---|---|---|
| ATOM | 3373 | CB | GLU P | 1 | .169 | 60.111 | 75.304 | 1.00 | 29.50 | P |
| ATOM | 3374 | CG | GLU P | 1 | −.450 | 58.935 | 76.069 | 1.00 | 30.79 | P |
| ATOM | 3375 | CD | GLU P | 1 | −1.151 | 57.917 | 75.185 | 1.00 | 31.68 | P |
| ATOM | 3376 | OE1 | GLU P | 1 | −.571 | 57.477 | 74.172 | 1.00 | 32.86 | P |
| ATOM | 3377 | OE2 | GLU P | 1 | 2.288 | 57.530 | 75.519 | 1.00 | 31.76 | P |
| ATOM | 3378 | C | GLU P | 1 | 2.442 | 59.065 | 75.475 | 1.00 | 27.76 | P |
| ATOM | 3379 | O | GLU P | 1 | 2.777 | 57.902 | 75.230 | 1.00 | 27.40 | P |
| ATOM | 3380 | N | GLU P | 1 | 1.201 | 58.964 | 73.347 | 1.00 | 28.40 | P |
| ATOM | 3381 | CA | GLU P | 1 | 1.473 | 59.802 | 74.549 | 1.00 | 28.51 | P |
| ATOM | 3382 | N | LEU P | 2 | 2.882 | 59.739 | 76.537 | 1.00 | 27.14 | P |
| ATOM | 3383 | CA | LEU P | 2 | 3.825 | 59.156 | 77.497 | 1.00 | 26.40 | P |
| ATOM | 3384 | CB | LEU P | 2 | 4.343 | 60.235 | 78.462 | 1.00 | 26.88 | P |
| ATOM | 3385 | CG | LEU P | 2 | 5.264 | 61.329 | 77.913 | 1.00 | 27.33 | P |
| ATOM | 3386 | CD1 | LEU P | 2 | 5.473 | 62.406 | 78.981 | 1.00 | 27.63 | P |
| ATOM | 3387 | CD2 | LEU P | 2 | 6.590 | 60.720 | 77.491 | 1.00 | 27.68 | P |
| ATOM | 3388 | C | LEU P | 2 | 3.239 | 58.008 | 78.317 | 1.00 | 25.81 | P |
| ATOM | 3389 | O | LEU P | 2 | 2.049 | 58.000 | 78.625 | 1.00 | 25.51 | P |
| ATOM | 3390 | N | ASP P | 3 | 4.089 | 57.047 | 78.676 | 1.00 | 24.98 | P |
| ATOM | 3391 | CA | ASP P | 3 | 3.676 | 55.898 | 79.480 | 1.00 | 24.32 | P |
| ATOM | 3392 | CB | ASP P | 3 | 4.873 | 54.973 | 79.733 | 1.00 | 23.70 | P |
| ATOM | 3393 | CG | ASP P | 3 | 4.531 | 53.803 | 80.642 | 1.00 | 23.27 | P |
| ATOM | 3394 | OD1 | ASP P | 3 | 3.595 | 53.040 | 80.302 | 1.00 | 22.76 | P |
| ATOM | 3395 | OD2 | ASP P | 3 | 5.191 | 53.643 | 81.693 | 1.00 | 21.86 | P |
| ATOM | 3396 | C | ASP P | 3 | 3.109 | 56.356 | 80.824 | 1.00 | 24.44 | P |
| ATOM | 3397 | O | ASP P | 3 | 3.351 | 57.484 | 81.263 | 1.00 | 24.24 | P |
| ATOM | 3398 | N | LYS P | 4 | 2.380 | 55.466 | 81.489 | 1.00 | 24.58 | P |
| ATOM | 3399 | CA | LYS P | 4 | 1.784 | 55.778 | 82.784 | 1.00 | 25.00 | P |
| ATOM | 3400 | CB | LYS P | 4 | 1.079 | 54.543 | 83.350 | 1.00 | 24.68 | P |
| ATOM | 3401 | CG | LYS P | 4 | .247 | 54.779 | 84.613 | 1.00 | 24.80 | P |
| ATOM | 3402 | CD | LYS P | 4 | −.464 | 53.485 | 85.037 | 1.00 | 24.50 | P |
| ATOM | 3403 | CE | LYS P | 4 | −1.508 | 53.723 | 86.133 | 1.00 | 24.83 | P |
| ATOM | 3404 | NZ | LYS P | 4 | −2.572 | 54.671 | 85.678 | 1.00 | 24.26 | P |
| ATOM | 3405 | C | LYS P | 4 | 2.816 | 56.253 | 83.806 | 1.00 | 25.53 | P |
| ATOM | 3406 | O | LYS P | 4 | 2.528 | 57.124 | 84.622 | 1.00 | 25.08 | P |
| ATOM | 3407 | N | TRP P | 5 | 4.020 | 55.693 | 83.753 | 1.00 | 25.97 | P |

TABLE 4-continued

| ELDKWAS: | | | | | | | | | | |
|---|---|---|---|---|---|---|---|---|---|---|
| ATOM | 3408 | CA | TRP P | 5 | 5.030 | 56.046 | 84.743 | 1.00 | 27.09 | P |
| ATOM | 3409 | CB | TRP P | 5 | 5.639 | 54.756 | 85.307 | 1.00 | 26.62 | P |
| ATOM | 3410 | CG | TRP P | 5 | 4.580 | 53.754 | 85.684 | 1.00 | 26.36 | P |
| ATOM | 3411 | CD2 | TRP P | 5 | 3.646 | 53.863 | 86.766 | 1.00 | 26.15 | P |
| ATOM | 3412 | CE2 | TRP P | 5 | 2.774 | 52.752 | 86.682 | 1.00 | 25.96 | P |
| ATOM | 3413 | CE3 | TRP P | 5 | 3.461 | 54.795 | 87.798 | 1.00 | 26.24 | P |
| ATOM | 3414 | CD1 | TRP P | 5 | 4.247 | 52.607 | 85.006 | 1.00 | 26.28 | P |
| ATOM | 3415 | NE1 | TRP P | 5 | 3.164 | 52.003 | 85.602 | 1.00 | 25.88 | P |
| ATOM | 3416 | CZ2 | TRP P | 5 | 1.728 | 52.545 | 87.595 | 1.00 | 25.85 | P |
| ATOM | 3417 | CZ3 | TRP P | 5 | 2.415 | 54.593 | 88.706 | 1.00 | 26.20 | P |
| ATOM | 3418 | CH2 | TRP P | 5 | 1.564 | 53.477 | 88.597 | 1.00 | 25.91 | P |
| ATOM | 3419 | C | TRP P | 5 | 6.137 | 56.995 | 84.280 | 1.00 | 27.96 | P |
| ATOM | 3420 | O | TRP P | 5 | 7.123 | 57.182 | 84.985 | 1.00 | 27.77 | P |
| ATOM | 3421 | N | ALA P | 6 | 5.967 | 57.598 | 83.107 | 1.00 | 29.24 | P |
| ATOM | 3422 | CA | ALA P | 6 | 6.957 | 58.534 | 82.571 | 1.00 | 30.79 | P |
| ATOM | 3423 | CB | ALA P | 6 | 6.738 | 58.733 | 81.077 | 1.00 | 30.55 | P |
| ATOM | 3424 | C | ALA P | 6 | 6.919 | 59.890 | 83.277 | 1.00 | 32.11 | P |
| ATOM | 3425 | O | ALA P | 6 | 5.904 | 60.273 | 83.848 | 1.00 | 32.54 | P |
| ATOM | 3426 | N | SER P | 7 | 8.040 | 60.601 | 83.213 | 1.00 | 33.55 | P |
| ATOM | 3427 | CA | SER P | 7 | 8.206 | 61.923 | 83.812 | 1.00 | 35.02 | P |
| ATOM | 3428 | CB | SER P | 7 | 7.007 | 62.821 | 83.481 | 1.00 | 35.56 | P |
| ATOM | 3429 | OG | SER P | 7 | 6.922 | 63.058 | 82.085 | 1.00 | 36.31 | P |
| ATOM | 3430 | C | SER P | 7 | 8.388 | 61.868 | 85.317 | 1.00 | 35.70 | P |
| ATOM | 3431 | O | SER P | 7 | 9.555 | 61.945 | 85.772 | 1.00 | 35.92 | P |
| ATOM | 3432 | OT | SER P | 7 | 7.357 | 61.724 | 86.013 | 1.00 | 36.58 | P |

TABLE 5

| ELDRWAS: | | | | | | | | | | |
|---|---|---|---|---|---|---|---|---|---|---|
| ATOM | 3265 | CB | GLU P | 1 | .001 | 59.852 | 75.796 | 1.00 | 71.00 | P |
| ATOM | 3266 | CG | GLU P | 1 | −.479 | 58.562 | 76.462 | 1.00 | 71.58 | P |
| ATOM | 3267 | CD | GLU P | 1 | −1.144 | 57.609 | 75.494 | 1.00 | 71.95 | P |
| ATOM | 3268 | OE1 | GLU P | 1 | −.554 | 57.311 | 74.431 | 1.00 | 72.48 | P |
| ATOM | 3269 | OE2 | GLU P | 1 | −2.260 | 57.134 | 75.803 | 1.00 | 71.87 | P |
| ATOM | 3270 | C | GLU P | 1 | 2.326 | 58.990 | 75.760 | 1.00 | 36.82 | P |
| ATOM | 3271 | O | GLU P | 1 | 2.717 | 57.867 | 75.436 | 1.00 | 36.76 | P |
| ATOM | 3272 | N | GLU P | 1 | .985 | 59.009 | 73.662 | 1.00 | 37.23 | P |
| ATOM | 3273 | CA | GLU P | 1 | 1.270 | 59.720 | 74.941 | 1.00 | 37.14 | P |
| ATOM | 3274 | N | LEU P | 2 | 2.775 | 59.627 | 76.833 | 1.00 | 33.88 | P |
| ATOM | 3275 | CA | LEU P | 2 | 3.783 | 59.034 | 77.702 | 1.00 | 33.45 | P |
| ATOM | 3276 | CB | LEU P | 2 | 4.389 | 60.114 | 78.611 | 1.00 | 61.37 | P |
| ATOM | 3277 | CG | LEU P | 2 | 5.316 | 61.181 | 78.000 | 1.00 | 61.47 | P |
| ATOM | 3278 | CD1 | LEU P | 2 | 5.506 | 62.346 | 78.978 | 1.00 | 61.51 | P |
| ATOM | 3279 | CD2 | LEU P | 2 | 6.659 | 60.540 | 77.642 | 1.00 | 61.59 | P |
| ATOM | 3280 | C | LEU P | 2 | 3.249 | 57.876 | 78.568 | 1.00 | 33.17 | P |
| ATOM | 3281 | O | LEU P | 2 | 2.140 | 57.937 | 79.109 | 1.00 | 32.99 | P |
| ATOM | 3282 | N | ASP P | 3 | 4.054 | 56.821 | 78.684 | 1.00 | 36.78 | P |
| ATOM | 3283 | CA | ASP P | 3 | 3.700 | 55.666 | 79.496 | 1.00 | 36.51 | P |
| ATOM | 3284 | CE | ASP P | 3 | 4.892 | 54.727 | 79.664 | 1.00 | 27.42 | P |
| ATOM | 3285 | CG | ASP P | 3 | 4.583 | 53.569 | 80.597 | 1.00 | 27.10 | P |
| ATOM | 3286 | OD1 | ASP P | 3 | 3.676 | 52.778 | 80.258 | 1.00 | 26.93 | P |
| ATOM | 3287 | OD2 | ASP P | 3 | 5.235 | 53.460 | 81.668 | 1.00 | 26.53 | P |
| ATOM | 3288 | C | ASP P | 3 | 3.285 | 56.155 | 80.868 | 1.00 | 36.57 | P |
| ATOM | 3289 | O | ASP P | 3 | 3.595 | 57.280 | 81.245 | 1.00 | 36.49 | P |
| ATOM | 3290 | N | ARG P | 4 | 2.628 | 55.288 | 81.629 | 1.00 | 47.13 | P |
| ATOM | 3291 | CA | ARG P | 4 | 2.150 | 55.639 | 82.957 | 1.00 | 47.37 | P |
| ATOM | 3292 | CB | ARG P | 4 | 1.309 | 54.495 | 83.516 | 1.00 | 57.30 | P |
| ATOM | 3293 | CG | ARG P | 4 | .545 | 54.865 | 84.764 | 1.00 | 57.28 | P |
| ATOM | 3294 | CD | ARG P | 4 | −.201 | 53.678 | 85.351 | 1.00 | 57.26 | P |
| ATOM | 3295 | NE | ARG P | 4 | −1.066 | 54.115 | 86.436 | 1.00 | 50.30 | P |
| ATOM | 3296 | CZ | ARG P | 4 | −1.736 | 53.309 | 87.256 | 1.00 | 50.30 | P |
| ATOM | 3297 | NH1 | ARG P | 4 | −1.646 | 51.994 | 87.118 | 1.00 | 50.30 | P |
| ATOM | 3298 | NH2 | ARG P | 4 | −2.495 | 53.822 | 88.227 | 1.00 | 50.30 | P |
| ATOM | 3299 | C | ARG P | 4 | 3.238 | 56.014 | 83.971 | 1.00 | 47.65 | P |
| ATOM | 3300 | O | ARG P | 4 | 3.016 | 56.861 | 84.840 | 1.00 | 47.39 | P |
| ATOM | 3301 | N | TRP P | 5 | 4.412 | 55.402 | 83.873 | 1.00 | 41.46 | P |
| ATOM | 3302 | CA | TRP P | 5 | 5.460 | 55.724 | 84.829 | 1.00 | 41.97 | P |
| ATOM | 3303 | CB | TRP P | 5 | 6.039 | 54.431 | 85.387 | 1.00 | 45.39 | P |
| ATOM | 3304 | CG | TRP P | 5 | 4.981 | 53.415 | 85.744 | 1.00 | 45.32 | P |
| ATOM | 3305 | CD2 | TRP P | 5 | 4.092 | 53.454 | 86.870 | 1.00 | 45.24 | P |
| ATOM | 3306 | CE2 | TRP P | 5 | 3.257 | 52.319 | 86.781 | 1.00 | 45.24 | P |
| ATOM | 3307 | CE3 | TRP P | 5 | 3.920 | 54.340 | 87.948 | 1.00 | 45.31 | P |
| ATOM | 3308 | CD1 | TRP P | 5 | 4.655 | 52.292 | 85.041 | 1.00 | 45.27 | P |

TABLE 5-continued

| ELDRWAS: | | | | | | | | | | |
|---|---|---|---|---|---|---|---|---|---|---|
| ATOM | 3309 | NE1 | TRP P | 5 | 3.623 | 51.627 | 85.657 | 1.00 | 45.13 | P |
| ATOM | 3310 | CZ2 | TRP P | 5 | 2.266 | 52.044 | 87.724 | 1.00 | 45.22 | P |
| ATOM | 3311 | CZ3 | TRP P | 5 | 2.931 | 54.064 | 88.891 | 1.00 | 45.30 | P |
| ATOM | 3312 | CH2 | TRP P | 5 | 2.117 | 52.924 | 88.769 | 1.00 | 45.34 | P |
| ATOM | 3313 | C | TRP P | 5 | 6.582 | 56.618 | 84.264 | 1.00 | 42.36 | P |
| ATOM | 3314 | O | TRP P | 5 | 7.669 | 56.695 | 84.834 | 1.00 | 42.32 | P |
| ATOM | 3315 | N | ALA P | 6 | 6.296 | 57.305 | 83.157 | 1.00 | 47.84 | P |
| ATOM | 3316 | CA | ALA P | 6 | 7.267 | 58.192 | 82.512 | 1.00 | 48.51 | P |
| ATOM | 3317 | CB | ALA P | 6 | 6.977 | 58.286 | 81.026 | 1.00 | 39.87 | P |
| ATOM | 3318 | C | ALA P | 6 | 7.290 | 59.597 | 83.117 | 1.00 | 49.00 | P |
| ATOM | 3319 | O | ALA P | 6 | 6.372 | 60.000 | 83.838 | 1.00 | 49.16 | P |
| ATOM | 3320 | N | SER P | 7 | 8.349 | 60.336 | 82.795 | 1.00 | 52.63 | P |
| ATOM | 3321 | CA | SER P | 7 | 8.551 | 61.700 | 83.282 | 1.00 | 53.25 | P |
| ATOM | 3322 | CB | SER P | 7 | 7.283 | 62.531 | 83.064 | 1.00 | 91.37 | P |
| ATOM | 3323 | OG | SER P | 7 | 7.464 | 63.854 | 83.541 | 1.00 | 91.74 | P |
| ATOM | 3324 | C | SER P | 7 | 8.937 | 61.727 | 84.765 | 1.00 | 53.52 | P |
| ATOM | 3325 | O | SER P | 7 | 10.153 | 61.808 | 85.062 | 1.00 | 53.79 | P |
| ATOM | 3326 | OT | SER P | 7 | 8.026 | 61.637 | 85.617 | 1.00 | 92.11 | P |

REFERENCES

1. Muster, T., et al., A conserved neutralizing epitope on gp41 of human immunodeficiency virus type 1, J. Virol., 67, 6642-6647 (1993).
2. Muster, T., et al., Cross-neutralizing activity against divergent human immunodeficiency virus type 1 isolates induced by the gp41 sequence ELDKWAS. J. virology, 68, 4031-4034 (1994).
3. Purtscher, M., et al., A broadly neutralizing human monoclonal antibody against pg41 of human immunodeficiency virus type 1 (HIV-1) AIDS Res. And Human Retroviruses, 10, 1651-1658 (1994).
4. Conley, A. J., et al., Neutralization of divergent human immunodefidiciency virus type I varints and primary isolates by IAM-41-2F5, an anti-gp41 human monoclonal antibody. Proc. Natl. Acad. Sci. USA, 91, 3348-3352 (1994).
5. Trkola, A., et al., Cross-clade neutralization of primary isolates of human immunodeficiency virus type 1 by human monoclonal antibodies and tetrameric CD4-IGG. J. Virology, 69, 6609-6617 (1995).
6. Burton D. R., A vaccine for HIV type 1: The antibody perspective. Proc. Natl. Acad. Sci. USA, 94, 10018-10023 (1997).
7. Mascola, J. R., et al. Potent and synergistic Neutralization of human immunodeficiency virus (HIV) type 1 primary isolates by hyperimmune anti-HIV immunolobulin combined with monoclonal antibodies 2F5 and 2G12. J. Virology, 71, 7198-7206 (1997).
8. Eckhart, L., et al., Immunogenic presentation of a conserved gp41 epitope of human immunodeficiency virus type 1 on recombinant surface antigens of hepatitus B. virus. J. of General Virology, 77, 2001-2008 (1996).
9. Kunert, R., et al., Molecular characterization of five neutralizing anti-HIV type 1 antibodies: identification of nonoconventional D segments in the human monoclonal antibodies 2G12 and 2F5, AIDS Res. and Human Retroviruses, 14, 1115-1128, (1998).
10. Richardson, J. S., The anatomy and taxonomy of protein structure, Adv. Protein Chem., 34, 167-339, (1981).
11. HIV Sequence Database, Los Alamos National Laboratory, Theoretical Biology and Biophysics Group T-10, Los Alamos, New Mexico.
12. Nicholls, A., Honig, B., "GRASP", Columbia University.
13. Gallaher, W. R., et al., A general model for the transmembrane proteins of HIV and other retroviruses. AIDS Res. And Human Retroviruses, 5, 431-440 (1989).
14. Weissenhom, W., et al., Atomic structure of the ectodomain from HIV-1 gp41. Nature, 387, 426-430 (1997).
15. Tan, K., et al., Atomic structure of a thermostable subdomain of HIV-1 gp41. Proc. Natl. Acad. Sci. USA, 94, 12303-12308 (1997).
16. Chan, d., et al., Core structure of gp41 from the HIV envleope glycoprotein. Cell, 89, 263-273 (1997).
17. Malashkevich, V. N., et al., Crystal structure of the simian immunodeficiency virus (SI) gp41 core: Conserved helical interactions underlie the broad inhibitory activity of gp41 peptides, Proc. Natl. Acad. Sci. USA, 95, 9134-9139 (1998).
18. Yang, Z. N., et al., High resolution structure of simian immunodeficiency virus gp41 ectodomain, Abstracts, American Crystallographic Association Annual Meeting, 1998.
19. Caffrey, M., et al., Three-dimensional solution structure of the 44 kDa ectodomain of SIV gp41, the EMBO J., 17, 4572-4584 (1998).
20. Lim L., et al., The three-dimensional structure of glutathione-S-transferase of Schistosoma japonicum fused with a conserved neutralizing epitope of human immunodeficiency virus type 1. Protein Science, 3, 2233-2244 (1994).
21. Ernst W., et al., Baculovirus surface display: Construction and screenign of a eukaryotic epitope library, Nucl. Acids Res. 26, 1718-1723 (1998).
22. Cook, J., et al., Recombinant antibodies with conformationally constrained HIV type 1 epitope inserts elicit glycoprotein 160-specific antibody responses in vivo. AIDS Res. Human Retroviruses, 13, 449-460 (1997).
23. Chan, D. E. & Kim, P. S., HIV entry and its inhibition, Cell, 93, 681-684 (1998).
24. Navaza, J., AMoRe- an automated package for molecular replacement, Acta Crystallogr., A50, 157-163 (1994).

25. Jeffrey, P. D., et al., The X-ray structure of anti-tumour antibody in complex with antigen. Nature Struct. Biol., 2, 466-471 (1995).
26. Brunger, A. T., et al., Crystallography and NMR system: A new software system for macromolecular structure determination, Acta Cryst. D, 54, 905-921 (1998).
27. Kraulis, P. J., MOLSCRIPT: a program to produce both detailed and schematic plots of protein structure, J., Applied Cryst., 24, 946-950 (1991).
28. Merritt, E. A. & Murphy, M. E. P. Raster 3D Version 2.0, A program for photoreolislic Molecular graphics. Acta Cryst. D50, 869-873, (1994).
29. Jones, T. A. et al., Acta Cryst. D47, 110-119 (1991).
30. Evans, S. V., SETOR: hardware-lighted three-dimensional solid model representations of macromolecules, J. Mol. Graph., 11, 134-8, (1993).
31. Ridles et al., (1983), Methods Enzym. 91:49-60.
32. Chong et al., (1991), Mol. Immunol. 28: 239-245.

What we claim is:

1. An isolated synthetic peptide wherein said peptide has the amino acid sequence ECDKWCS (SEQ ID No.: 3) and has a disulphide bridge between the cysteine residues at positions 2 and 6 of SEQ ID No.:3.

2. The synthetic peptide of claim 1 which is linked to a carrier protein.

3. An isolated synthetic peptide wherein said peptide has the formula EdapDKWES (SEQ ID No.:4) and has a lactam bond between the diaminopropionic acid (dap) and glutamate at position 6 of SEQ ID No.:4.

4. The synthetic peptide of claim 3 which is linked to a carrier protein.

* * * * *

SEQUENCE LISTING

```
<160> NUMBER OF SEQ ID NOS: 11

<210> SEQ ID NO 1
<211> LENGTH: 7
<212> TYPE: PRT
<213> ORGANISM: Human immunodeficiency virus type 1

<400> SEQUENCE: 1

Glu Leu Asp Lys Trp Ala Ser
  1               5


<210> SEQ ID NO 2
<211> LENGTH: 7
<212> TYPE: PRT
<213> ORGANISM: Human immunodeficiency virus type 1

<400> SEQUENCE: 2

Glu Leu Asp Arg Trp Ala Ser
  1               5


<210> SEQ ID NO 3
<211> LENGTH: 7
<212> TYPE: PRT
<213> ORGANISM: Human immunodeficiency virus type 1

<400> SEQUENCE: 3

Glu Cys Asp Lys Trp Cys Ser
  1               5


<210> SEQ ID NO 4
<211> LENGTH: 7
<212> TYPE: PRT
<213> ORGANISM: Human immunodeficiency virus type 1
<220> FEATURE:
<221> NAME/KEY: misc_feature
<222> LOCATION: 2
<223> OTHER INFORMATION: Xaa equals Diaminopropionic acid (dap)

<400> SEQUENCE: 4

Glu Xaa Asp Lys Trp Glu Ser
  1               5


<210> SEQ ID NO 5
<211> LENGTH: 7
<212> TYPE: PRT
<213> ORGANISM: Human immunodeficiency virus type 1
<220> FEATURE:
<221> NAME/KEY: misc_feature
<222> LOCATION: 6
<223> OTHER INFORMATION: Xaa equals Diaminopropionic acid (dap)

<400> SEQUENCE: 5

Glu Glu Asp Lys Trp Xaa Ser
  1               5
```

-continued

```
<210> SEQ ID NO 6
<211> LENGTH: 214
<212> TYPE: PRT
<213> ORGANISM: Human immunodeficiency virus type 1

<400> SEQUENCE: 6

Ala Leu Gln Leu Thr Gln Ser Pro Ser Ser Leu Ser Ala Ser Val Gly
  1               5                  10                  15

Asp Arg Ile Thr Ile Thr Cys Arg Ala Ser Gln Gly Val Thr Ser Ala
             20                  25                  30

Leu Ala Trp Tyr Arg Gln Lys Pro Gly Ser Pro Pro Gln Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Glu Phe Thr Leu Thr Ile Ser Thr Leu Arg Pro
 65                  70                  75                  80

Glu Asp Phe Ala Thr Tyr Tyr Cys Gln Gln Leu His Phe Tyr Pro His
                 85                  90                  95

Thr Phe Gly Gly Gly Thr Arg Val Asp Val Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 7
<211> LENGTH: 462
<212> TYPE: PRT
<213> ORGANISM: Human immunodeficiency virus type 1

<400> SEQUENCE: 7

Arg Ile Thr Leu Lys Glu Ser Gly Pro Pro Leu Val Lys Pro Thr Gln
  1               5                  10                  15

Thr Leu Thr Leu Thr Cys Ser Phe Ser Gly Phe Ser Leu Ser Asp Phe
             20                  25                  30

Gly Val Gly Val Gly Trp Ile Arg Gln Pro Pro Gly Lys Ala Leu Glu
         35                  40                  45

Trp Leu Ala Ile Ile Tyr Ser Asp Asp Asp Lys Arg Tyr Ser Pro Ser
     50                  55                  60

Leu Asn Thr Arg Leu Thr Ile Thr Lys Asp Thr Ser Lys Asn Gln Val
 65                  70                  75                  80

Val Leu Val Met Thr Arg Val Ser Pro Val Asp Thr Ala Thr Tyr Phe
                 85                  90                  95

Cys Ala His Arg Arg Gly Pro Thr Thr Leu Phe Gly Val Pro Ile Ala
            100                 105                 110
```

-continued

```
Arg Gly Pro Val Asn Ala Met Asp Val Trp Gly Gln Gly Ile Thr Val
        115                 120                 125

Thr Ile Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Phe Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 8
<211> LENGTH: 7
<212> TYPE: PRT
<213> ORGANISM: Human immunodeficiency virus type 1
<220> FEATURE:
<221> NAME/KEY: misc_feature
<222> LOCATION: 1
<223> OTHER INFORMATION: Xaa equals Glutamic acid, Alanine, Glycine or
Glutamine
<220> FEATURE:
<221> NAME/KEY: misc_feature
<222> LOCATION: 6

-continued

```
<223> OTHER INFORMATION: Xaa equals Alanine or Threonine

<400> SEQUENCE: 8

Xaa Leu Asp Lys Trp Xaa Ser
  1               5


<210> SEQ ID NO 9
<211> LENGTH: 4
<212> TYPE: PRT
<213> ORGANISM: Human immunodeficiency virus type 1

<400> SEQUENCE: 9

Leu Asp Lys Trp
  1


<210> SEQ ID NO 10
<211> LENGTH: 4
<212> TYPE: PRT
<213> ORGANISM: Human immunodeficiency virus type 1

<400> SEQUENCE: 10

Cys Gly Gly Gly
  1


<210> SEQ ID NO 11
<211> LENGTH: 4
<212> TYPE: PRT
<213> ORGANISM: Human immunodeficiency virus type 1

<400> SEQUENCE: 11

Gly Gly Gly Cys
  1
```